United States Patent
Santos et al.

(10) Patent No.: US 11,605,162 B2
(45) Date of Patent: Mar. 14, 2023

(54) SYSTEMS AND METHODS FOR DETERMINING A FLUID AND TISSUE VOLUME ESTIMATIONS USING ELECTRICAL PROPERTY TOMOGRAPHY

(71) Applicant: Timpel Medical B.V., Eindhoven (NL)

(72) Inventors: Talles Batista Rattis Santos, Sao Paulo (BR); Rafael Mikio Nakanishi, Sao Paulo (BR)

(73) Assignee: Timpel B.V., Eindhoven (NL)

( * ) Notice: Subject to any disclaimer, the term of this patent is extended or adjusted under 35 U.S.C. 154(b) by 180 days.

(21) Appl. No.: 16/947,146

(22) Filed: Jul. 21, 2020

(65) Prior Publication Data
US 2021/0027461 A1    Jan. 28, 2021

Related U.S. Application Data

(60) Provisional application No. 62/880,548, filed on Jul. 30, 2019, provisional application No. 62/878,097, filed on Jul. 24, 2019.

(51) Int. Cl.
G06T 7/00 (2017.01)
G06T 7/62 (2017.01)
(Continued)

(52) U.S. Cl.
CPC .......... G06T 7/0012 (2013.01); A61B 5/0535 (2013.01); A61B 5/0809 (2013.01);
(Continued)

(58) Field of Classification Search
None
See application file for complete search history.

(56) References Cited

U.S. PATENT DOCUMENTS

2003/0233039 A1* 12/2003 Shao ............... A61B 6/037
600/407
2004/0006279 A1* 1/2004 Arad (Abboud) ... A61B 5/0536
600/506
(Continued)

OTHER PUBLICATIONS

Detection of local lung air content by electrical impedance tomography compared with electron beam CT, Inéz Frerichs, José Hinz, Peter Herrmann, Gerald Weisser, Günter Hahn, Taras Dudykevych, Michael Quintel, and Gerhard Hellige, Journal of Applied Physiology 2002 93:2, 660-666 (Year: 2002).*

(Continued)

*Primary Examiner* — Vu Le
*Assistant Examiner* — Courtney Joan Nelson
(74) *Attorney, Agent, or Firm* — TraskBritt

(57) ABSTRACT

A system includes an electrical tomography system and a volume estimation system. The volume estimation system is configured to reconstruct an initial impedance image based at least partially on received electrical tomography data of a domain, receive prior information associated with the domain, enhance the initial impedance image based at least partially on the received prior information to generate an enhanced impedance image, and based at least partially on the enhanced initial impedance image, generate a volumetric image of a region of interest of the enhanced impedance image, wherein the volumetric image represents a plurality of values indicating a volume of a fluid.

22 Claims, 17 Drawing Sheets

(51) Int. Cl.
*G06T 7/11* (2017.01)
*A61B 5/0535* (2021.01)
*A61B 5/08* (2006.01)
*A61B 5/091* (2006.01)
*G06T 11/00* (2006.01)
*G06V 10/25* (2022.01)

(52) U.S. Cl.
CPC ............... *A61B 5/091* (2013.01); *G06T 7/11* (2017.01); *G06T 7/62* (2017.01); *G06T 11/008* (2013.01); *G06V 10/25* (2022.01); *A61B 2576/02* (2013.01); *G06T 2207/10081* (2013.01); *G06T 2207/30061* (2013.01)

(56) References Cited

U.S. PATENT DOCUMENTS

2008/0292169 A1   11/2008   Wang et al.
2010/0228143 A1*  9/2010   Teschner .............. A61B 5/0536
                                                                600/547

OTHER PUBLICATIONS

Martins Thiago De Castro et al, "A review of electrical impedance tomography in lung application: Theory and algorithms for absolute images", Annual Reviews in Control, Pergamon, Amsterdam, NL, vol. 48, Jan. 1, 2019 (Jan. 1, 2019), pp. 442-471 (Year: 2019).*

Adler et al.,"Monitoring changes in lung air and liquid volumes with electrical impedance tomography", J. Appl. Physiol, vol. 83, No. 5, Jan. 1, 1997 (Jan. 1, 1997), pp. 1762-1767 (Year: 1997).*

Sadleir, Rosalind J., and Richard A. Fox. "Detection and quantification of intraperitoneal fluid using electrical impedance tomography." IEEE transactions on biomedical engineering 48.4 (2001): 484-491. (Year: 2001).*

Dodd M, Mueller JL. A Real-time D-bar Algorithm for 2-D Electrical Impedance Tomography Data. Inverse Probl Imaging (Springfield). Nov. 1, 2014;8(4):1013-1031. doi: 10.3934/ipi.2014.8.1013. PMID: 25937856; PMCID: PMC4414053. (Year: 2014).*

Adler et al.,"Monitoring changes in lung air and liquid volumes with elecliical impedance tomography", J. Appl. Physiol, vol. 83, No. 5, Jan. 1, 1997 (Jan. 1, 1997), pp. 1762-1767.

Batista Rattis Santos et al.,"Introduction of sample based prior into the D-bar method through a Schur complement property", Journal of Latex Class Filed, vol. XX, No. XX, Jan. 2020, 9 pages.

International Search Report for Application No. PCT/IB2020/056851, dated Oct. 8, 2020, 5 pages.

Martine Thiago De Castro et al, "A review of electrical impedance tomography in lung application: Theory and algorithms for absolute images", Annual Reviews in Control, Pergamon, Amsterdam, NL, vol. 48, Jan. 1, 2019 (Jan. 1, 2019), pp. 442-471.

Melany Dodd et al., "A Real-time D-bar Algorithm for 2-D Electrical Impedance Tomography Data", , Inverse Probl Imaging (Springfield). Nov. 1, 2014;8(4):1013-1031.

Written Opinion of the International Searching Authority for Application No. PCT/IB2020/056851, dated Oct. 8, 2020, 10 pages.

* cited by examiner

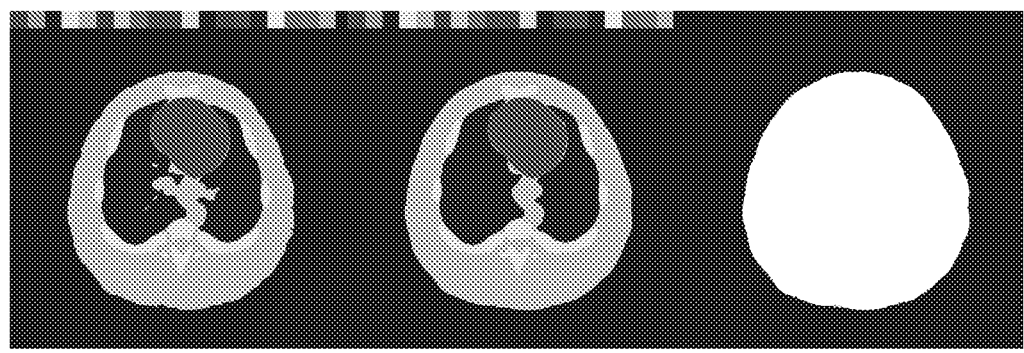
FIG. 10
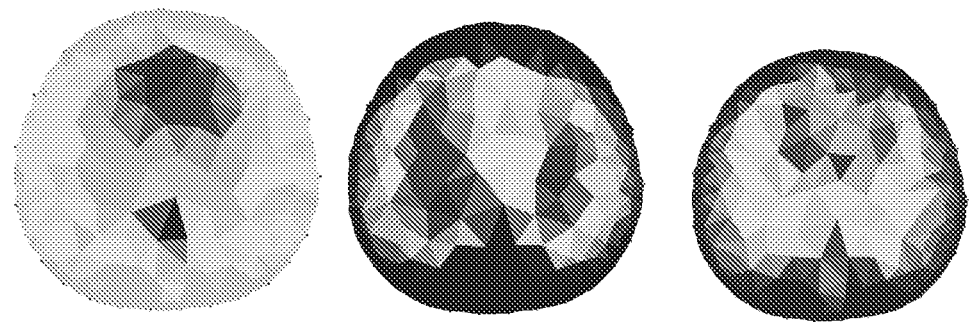
| 0.0409    0.272    0.503 | 0.00602    0.283    0.558 | 22.1    36    50 |
| (a) Mean | (b) Diagonal of the cov. matrix | (c) Diagonal of the inverse of cov. matrix |
| FIG. 11A | FIG. 11B | FIG. 11C |

(a) Front View  (b) Top View  (c) Side View (a) Front View  (b) Top View  (c) Side View

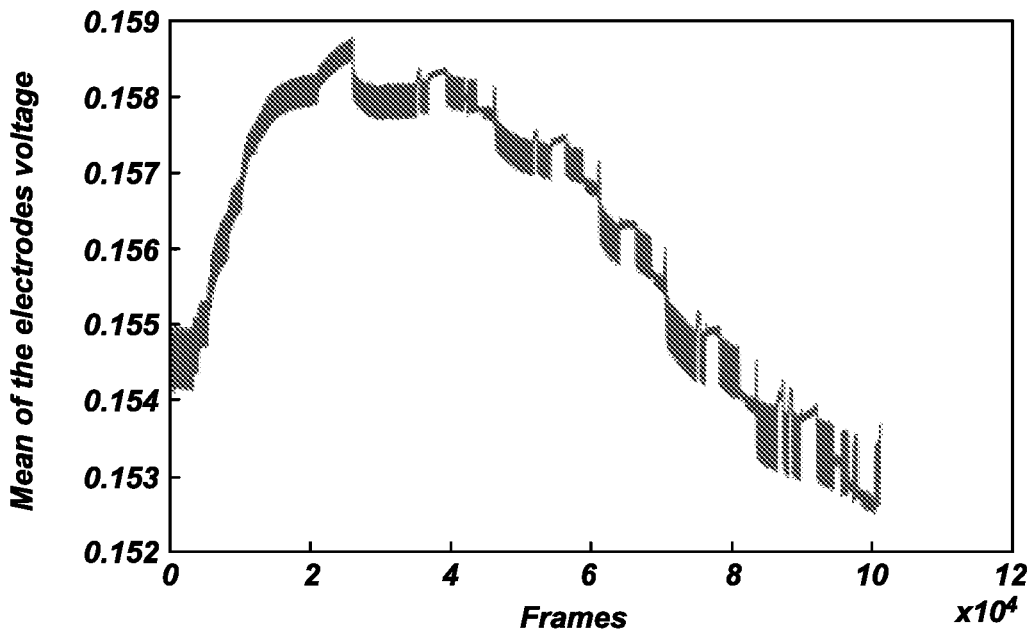
FIG. 14
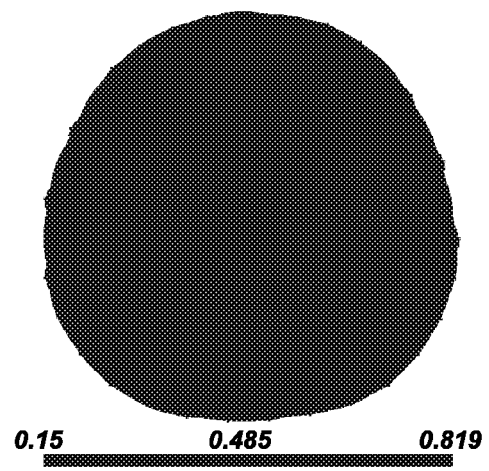
(a) Ct-scan, center of the belt
(b) Reconstructed image
FIG. 15
FIG. 16

0.15   0.485   0.819

0.15   0.485   0.819

0.15   0.485   0.819

0.15   0.485   0.819

0.15   0.485   0.819

0.15   0.485   0.819

SYSTEMS AND METHODS FOR DETERMINING A FLUID AND TISSUE VOLUME ESTIMATIONS USING ELECTRICAL PROPERTY TOMOGRAPHY

CROSS-REFERENCE TO RELATED APPLICATIONS

This application claims the benefit under 35 U.S.C. § 119(e) of U.S. Provisional Patent Application Ser. No. 62/878,097, filed Jul. 24, 2019, and to U.S. Provisional Patent Application Ser. No. 62/880,548, filed Jul. 30, 2019, the disclosure of each of which is hereby incorporated herein in its entirety by this reference.

TECHNICAL FIELD

The disclosure relates to systems and method for determining absolute volume estimations. In particular, this disclosure relates to systems and methods that include and utilize an electrical property tomography (e.g., electrical impedance tomography (EIT)) system in determining absolute volume estimations.

BACKGROUND

Electrical Impedance Tomography (EIT) is a non-invasive imaging method that may be used to generate images of a region of interest of a domain (e.g., a patient) by collecting data using electrodes disposed along the perimeter of the region of interest. One conventional application of EIT includes clinical applications, in which tomographic images of the human body may be useful. For example, EIT is conventionally used to monitor cardio-respiratory systems, which may be particularly useful in patients under treatment in intensive care unit (ICU) environments.

During EIT procedures, electrical signals (e.g., electric currents) may be injected into a perimeter of the region of interest of the domain being imaged (e.g., a patient's torso). Electrical characteristics (e.g., voltages, electric potentials) resulting from the injected electrical signals may be collected at the perimeter of the region of interest. From the collected data, a map with an estimate of electrical properties (e.g., impedances) may be generated or reconstructed. EIT systems are often susceptible to reconstruction artifacts. In order to mitigate artifacts, the reconstruction of EIT images often employs differential reconstruction techniques, in which the generated images (e.g., differential images) utilize changes between the current property (e.g., impedance) map and a reference impedance map. While differential images are useful in several settings, certain medical diagnoses are limited without knowledge of the absolute property (e.g., impedance) map.

As noted above, current EIT methods generally focus on the production of differential images. The preference toward differential images is likely a result of the fact that direct calculation of absolute impedance values from EIT data relies on a linear or quasi-linear reconstruction method that often overestimates values of some pixels and underestimates the values of other pixels of the region of interest.

BRIEF SUMMARY

Some embodiments include a method of estimate a fluid volume. The method may include receiving electrical tomography data of a portion of a domain, reconstructing an initial impedance image based at least partially on the electrical tomography data, enhancing the initial impedance image to generate an enhanced impedance image, segmenting the enhanced impedance image to identify one or more tissues depicted within the enhance impedance image, selecting a region of interest within the enhanced impedance image, determining a relationship parameter that relates electrical properties represented within the region of interest of the enhanced impedance image with one or more properties of the region of interest, and estimating a fluid volume within the region of interest based at least partially on the relationship parameter and the enhanced impedance image.

Some embodiments include a system for estimating a fluid volume within a domain. The system may include an electrical tomography system and a volume estimation system. The fluid volume estimation system may include at least one processor and at least one non-transitory computer-readable storage medium storing instructions thereon that, when executed by the at least one processor, cause the volume estimation system to: reconstruct an initial impedance image based at least partially on received electrical tomography data of a domain, receive prior information associated with the domain, enhance the initial impedance image based at least partially on the received prior information to generate an enhanced impedance image, and based at least partially on the enhanced initial impedance image, generate a volumetric image of a region of interest of the enhanced impedance image, wherein the volumetric image represents a plurality of values indicating a volume of a fluid.

Some embodiments include a system for estimating a fluid volume within a domain. The system may include an electrical tomography system and a volume estimation system. The fluid volume estimation system may include at least one processor and at least one non-transitory computer-readable storage medium storing instructions thereon that, when executed by the at least one processor, cause the volume estimation system to: receive prior information associated with a domain, receive an initial impedance image of a portion of the domain from the electrical tomography system, enhance an initial impedance image based at least partially on the received prior information to generate an enhanced impedance image, and based at least partially on the enhanced initial impedance image, generate a volumetric image of a region of interest of the enhanced impedance image, wherein the volumetric image represents a plurality of values indicating a volume of a fluid.

BRIEF DESCRIPTION OF THE DRAWINGS

FIG. 10 shows example segmented and processed images according to one or more embodiments of the present disclosure;

FIGS. 11A-11C show generated prior information used to reconstruct impedance images using a Gauss-Newton method according to one or more embodiments of the present disclosure;

FIG. 14 shows example voltage measurements detected during an EIT process;

FIG. 15 shows an example computed tomography scan obtained from a domain during one or more processes described herein;

FIG. 16 shows a reconstructed initial impedance image reconstructed according to one or more embodiments of the present disclosure;

DETAILED DESCRIPTION

Figure 1:
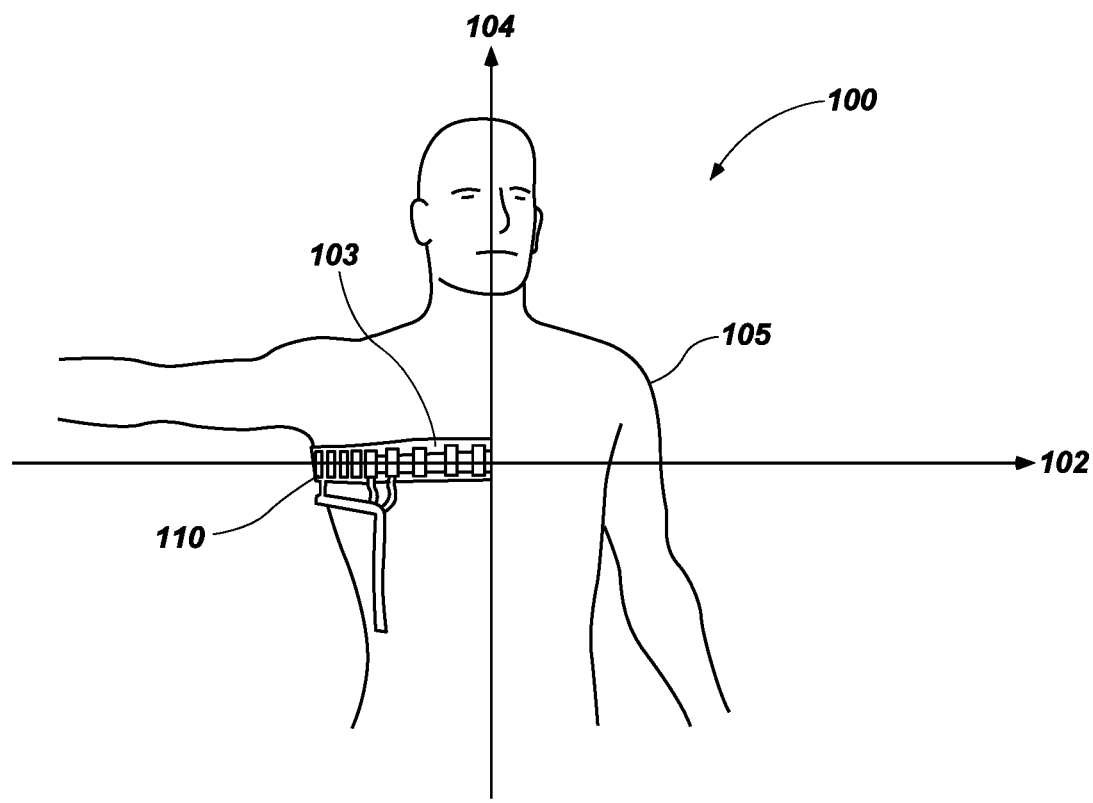
FIG. 1 is a schematic diagram of a portion of an electrical property tomography system showing a plurality of electrodes positioned around a region of interest of a patient according to one or more embodiments of the present disclosure.

The illustrations presented herein are not actual views of any EIT system or volume estimation system but are merely idealized representations employed to describe example embodiments of the disclosure. In the following detailed description, reference is made to the accompanying drawings which form a part hereof, and in which is shown by way of illustration specific embodiments in which the disclosure may be practiced. These embodiments are described in sufficient detail to enable those of ordinary skill in the art to practice the disclosure. It should be understood, however, that the detailed description and the specific examples, while indicating examples of embodiments of the disclosure, are given by way of illustration only and not by way of limitation. From this disclosure, various substitutions, modifications, additions rearrangements, or combinations thereof within the scope of the disclosure may be made and will become apparent to those of ordinary skill in the art.

In accordance with common practice, the various features illustrated in the drawings may not be drawn to scale. Accordingly, the dimensions of the various features may be arbitrarily expanded or reduced for clarity. In addition, some of the drawings may be simplified for clarity. Thus, the drawings may not depict all of the components of a given apparatus or all operations of a particular method.

Information and signals described herein may be represented using any of a variety of different technologies and techniques. For example, data, instructions, commands, information, signals, bits, symbols, and chips that may be referenced throughout the description may be represented by voltages, currents, electromagnetic waves, magnetic fields or particles, optical fields or particles, or any combination thereof. Some drawings may illustrate signals as a single signal for clarity of presentation and description. It should be understood by a person of ordinary skill in the art that the signal may represent a bus of signals, wherein the bus may have a variety of bit widths and the disclosure may be implemented on any number of data signals including a single data signal.

The various illustrative logical blocks, modules, and circuits described in connection with the embodiments disclosed herein may be implemented or performed with a general purpose processor, a special purpose processor, a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A general-purpose processor may be considered a special-purpose processor while the general-purpose processor executes instructions (e.g., software code) stored on a computer-readable medium. A processor may also be implemented as a combination of computing devices, e.g., a combination of a DSP and a microprocessor, a plurality of microprocessors, one or more microprocessors in conjunction with a DSP core, or any other such configuration.

Also, it is noted that embodiments may be described in terms of a process that may be depicted as a flowchart, a flow diagram, a structure diagram, or a block diagram. Although a flowchart may describe operational acts as a sequential process, many of these acts can be performed in another sequence, in parallel, or substantially concurrently. In addition, the order of the acts may be re-arranged. A process may correspond to a method, a function, a procedure, a subroutine, a subprogram, etc. Furthermore, the methods disclosed herein may be implemented in hardware, software, or both. If implemented in software, the functions may be stored or transmitted as one or more instructions or code on computer-readable media. Computer-readable media include both computer storage media and communication media, including any medium that facilitates transfer of a computer program from one place to another.

As used herein, the singular forms following "a," "an," and "the" are intended to include the plural forms as well, unless the context clearly indicates otherwise.

As used herein, the term "may" with respect to a material, structure, feature, or method act indicates that such is contemplated for use in implementation of an embodiment of the disclosure, and such term is used in preference to the more restrictive term "is" so as to avoid any implication that other compatible materials, structures, features, and methods usable in combination therewith should or must be excluded.

It should be understood that any reference to an element herein using a designation such as "first," "second," and so forth does not limit the quantity or order of those elements, unless such limitation is explicitly stated. Rather, these designations may be used herein as a convenient method of distinguishing between two or more elements or instances of an element. Thus, a reference to first and second elements does not mean that only two elements may be employed there or that the first element must precede the second element in some manner. Also, unless stated otherwise a set of elements may comprise one or more elements.

As used herein, the term "substantially" in reference to a given parameter, property, or condition means and includes to a degree that one skilled in the art would understand that the given parameter, property, or condition is met with a small degree of variance, such as within acceptable manufacturing tolerances. For example, a parameter that is substantially met may be at least about 90% met, at least about 95% met, or even at least about 99% met.

As used herein, the term "about" used in reference to a given parameter is inclusive of the stated value and has the meaning dictated by the context (e.g., it includes the degree of error associated with measurement of the given parameter, as well as variations resulting from manufacturing tolerances, etc.).

Embodiments of the disclosure include an electrical property tomography (e.g., electrical impedance tomography (EIT)) device and/or system for generating images of a region of a patient's body, and the images may be utilized to determine absolute volume estimations of a biological fluid (e.g., air, blood, water, tissue). For clarity and ease of explanation, EIT systems will be referenced herein throughout the disclosure; however, any electrical property tomography device may be utilized in place of or in addition to the EIT systems and is within the scope of the present disclosure. For example, the electrical property tomography device may include device that measure one or more electrical conductivity, electrical resistivity, electrical permittivity, electrical admitivity, or any other electrical property. In particular, EIT is an imaging technique involving the positioning electrodes via an electrode belt placed around a region of a patient's body (e.g., around the patient's chest for imaging of a lung), injecting electrical excitation signals through a pair of electrodes, and measuring the induced response signals detected by the other electrodes of the electrode belt. The EIT system may generate an image based on the voltage measurements indicating estimated impedance values throughout at least a portion of the region of the patient's body. In contrast with other imaging techniques, EIT is non-invasive and does not present exposure risks (e.g., radiation exposure risks) that can limit the number and frequency of monitoring actions (e.g., as with techniques such as X-rays). As a result, EIT is suitable for continuously monitoring the condition of the patient, with particular application to monitoring the patient's lungs as the measurements may be used to determine respiratory and hemodynamic parameters of the patient and monitor a real-time two/three dimensional image.

Embodiments of the present disclosure relate to electrical property tomography systems and methods of operation thereof that may be used to generate absolute impedance images and/or volumetric measurements (e.g., fluid volume estimations) from EIT data. For example, embodiments of the present disclosure may include systems capable of performing corrections and/or enhancements to absolute impedance images. In some embodiments, correcting and/or enhancing the absolute impedance images may include utilizing priors (e.g., prior information), datasets that include statistical distributions that correlate impedances and EIT data. The systems and methods may be used to provide important diagnostic parameters of, for example, respiratory dynamics that may not be easily obtained from differential EIT images. Conditions and parameters that may be measured with the systems and methods described herein include, but are not limited to, functional residual capacity (FRC), tidal volume, pneumothorax detection, and cellularity on pleural diffusions.

FIG. 1 is a schematic diagram of a portion of an electrical impedance tomography (EIT) system 100 showing a plurality of electrodes 110 positioned around a region of interest (e.g., thorax) of a patient 105. The electrodes 110 of the EIT system 100 may be physically held in place by an electrode belt 103. The placement of the electrodes 110 may be transverse to a cranial caudal axis 104 of the patient. Although the electrodes 110 are shown in FIG. 1 as being placed only partially around the patient 105, electrodes 110 may be placed around the entire patient 105 depending on the specific region of interest available or desired for measurement. Furthermore, the electrodes 110 may be oriented relative to one another in one or more parallel rows (e.g., planes), in one or more zigzag patterns (e.g., one or more lines having abrupt alternate turns), or in any combination thereof. The electrodes 110 may be operably coupled to a computing system (not shown) configured to control the operation of the electrodes 110 and perform reconstruction of an EIT image.

Figure 2:
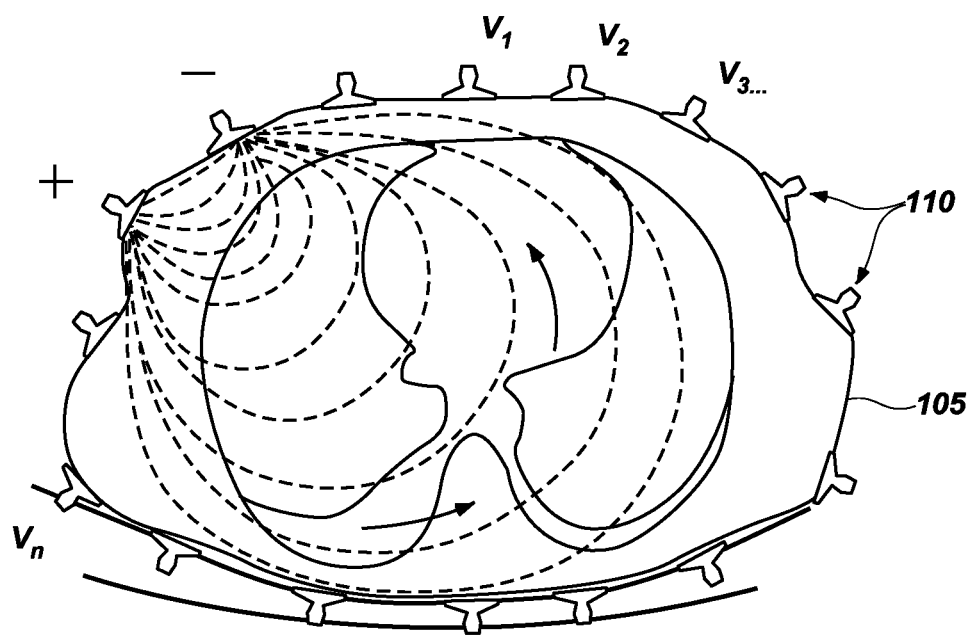
FIG. 2 is a schematic diagram showing a cross-section of the thorax of the patient along the plane of the electrodes according to one or more embodiments of the present disclosure.

FIG. 2 is a schematic diagram showing a cross-section of the thorax of the patient 105 along the plane (line 102) of the electrodes. A voltage may be applied to a pair of electrodes 110 (shown by the electrodes having a + and − symbol) to inject an excitation current into the patient between an electrode pair. As a result, voltages (e.g., $V_1, V_2, V_3 \ldots V_n$) may be detected by the other electrodes and measured by the EIT system 100. Current injection may be performed for a measurement cycle according to a circular pattern using different electrode pairs to generate the excitation current.

Figure 3:
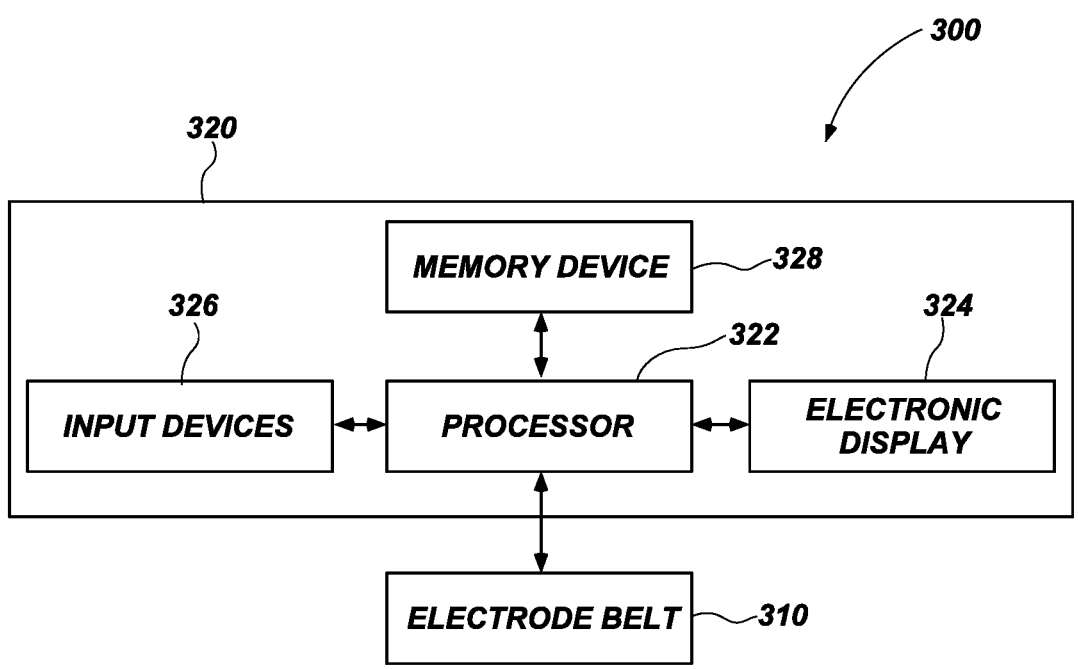
FIG. 3 is a schematic block diagram of an electrical property tomography system according to an embodiment of the disclosure.

FIG. 3 is a schematic block diagram of an EIT system 300 according to an embodiment of the disclosure. The EIT system 300 may include an electrode belt 310 operably coupled with a data processing system 320. The electrode belt 310 and the data processing system 320 may be coupled together via a wired connection (e.g., cables) and/or may have communication modules to communicate wirelessly with each other. The data processing system 320 may include a processor 322 operably coupled with an electronic display 324, input devices 326, and a memory device 328. The electronic display 324 may be constructed with the data processing system 320 into a singular form factor for an EIT device coupled with the electrode belt 310. In some embodiments, the electronic display 324 and the data processing system 320 may be separate units of the EIT device coupled with the electrode belt 310. In yet other embodiments, an EIT system 300 may be integrated within another host system configured to perform additional medical measurements and/or procedures, in which the electrode belt 310 may couple to a port of the host system already having its own input devices, memory devices, and electronic display.

As such, the host system may have the EIT processing software installed therein. Such software may be built into the host system prior field use or updated after installation.

The processor 322 may coordinate the communication between the various devices as well as execute instructions stored in computer-readable media of the memory device 328 to direct current excitation, data acquisition, data analysis, and/or image reconstruction. As an example, the memory device 328 may include a library of finite element meshes used by the processor 322 to model the patient's body in the region of interest for performing image reconstruction. Input devices 326 may include devices such as a keyboard, touch screen interface, computer mouse, remote control, mobile devices, or other devices that are configured to receive information that may be used by the processor 322 to receive inputs from an operator of the EIT system 300. Thus, for a touch screen interface the electronic display 324 and the input devices 326 receiving user input may be integrated within the same device. The electronic display 324 may be configured to receive the data and output the EIT image reconstructed by the processor for the operator to view. Additional data (e.g., numeric data, graphs, trend information, and other information deemed useful for the operator) may also be generated by the processor 322 from the measured EIT data alone, or in combination with other non-EIT data according to other equipment coupled thereto. Such additional data may be displayed on the electronic display 324.

The EIT system 300 may include components that are not shown in the figures, but may also be included to facilitate communication and/or current excitation with the electrode belt 310 as would be understood by one of ordinary skill in the art, such as including one or more analog to digital converter, signal treatment circuits, demodulation circuits, power sources, etc.

Figure 4:
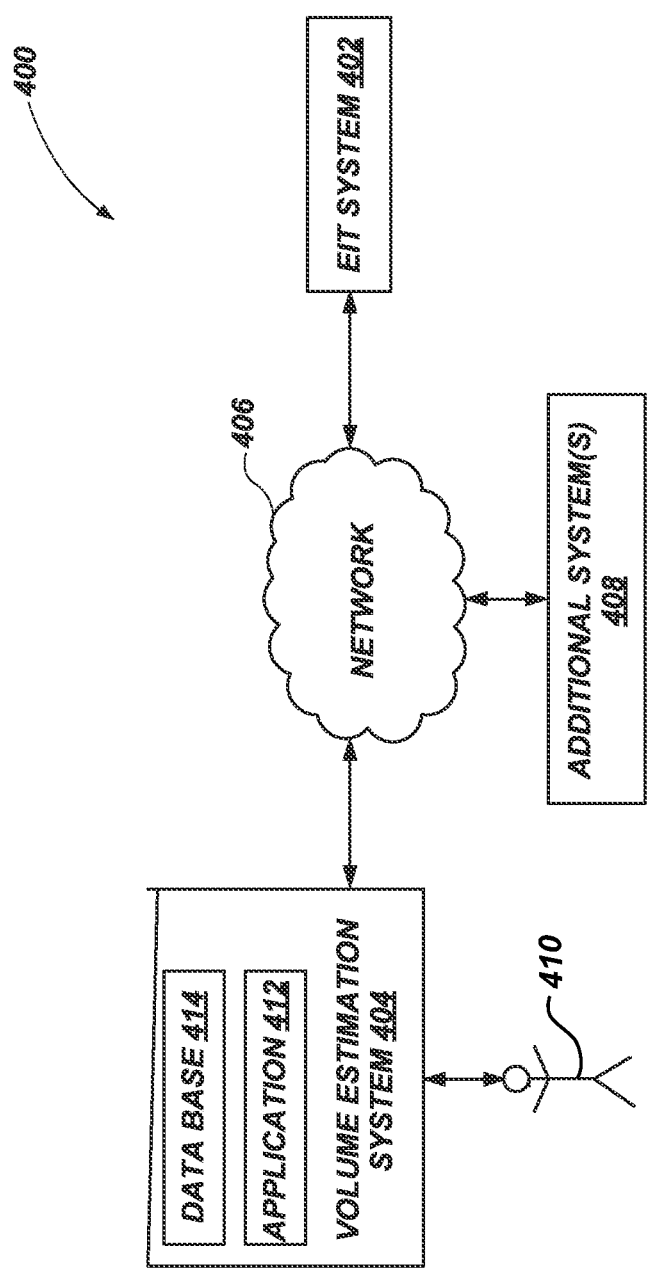
FIG. 4 illustrates a schematic diagram of an environment in which a volume estimation system can operate according to one or more embodiments of the present disclosure.

FIG. 4 illustrates a schematic diagram of an environment 400 in which a volume estimation system can operate according to one or more embodiments of the present disclosure. As illustrated, the environment 400 includes an EIT system 402, a volume estimation system 404, a network 406, and one or more additional system(s) 408. The volume estimation system 404, the EIT system 402, and the additional system(s) 408 can communicate via the network 406. The network 406 may include one or more networks, such as the Internet, and can use one or more communications platforms or technologies suitable for transmitting data and/or communication signals. Although FIG. 4 illustrates a particular arrangement of the EIT system 402, the volume estimation system 404, the additional system(s) 408, and the network 406, various additional arrangements are possible. For example, the volume estimation system 404 may directly communicate with the EIT system 402, bypassing the network 406.

As illustrated in FIG. 4, a user 410 can interface with the volume estimation system 404 to initiate one or more volume estimations and/or any of the methods described herein. The user 410 can be an individual (i.e., human user), a business, a group, or any other entity. Although FIG. 4 illustrates only one user 410 associated with the volume estimation system 404, the environment 400 can include any number of a plurality of users that each interact with the environment 400 using a corresponding volume estimation system 404.

In some embodiments, a volume estimation system 404 may include one or more types of servers, one or more data stores, one or more interfaces, including but not limited to APIs, one or more web services, one or more content sources, one or more networks, or any other suitable components, e.g., that servers may communicate with. In this sense, the volume estimation system 404 may provide a platform, or backbone, which other systems, such as the additional systems 408, may use to initiate fluid volume estimations within regions of interest of a domain (e.g., a patient).

In one or more embodiments, the volume estimation system 404 may perform reconstruction algorithms, correction algorithms, and/or volumetric calculation algorithms, as detailed below. In some embodiments, the volume estimation system 404 may also include an interface system for controlling the electrical signals going into and coming from electrical leads of an electrode belt of the EIT system 402. In one or more embodiments, the interface system may include, among other things, analog signal generators, analog-to-digital converters, digital-to-analog converters, digital signal processors, filters, and impedance matching circuitry, to improve signal-to-noise ratio and decrease crosstalk.

As shown in FIG. 4, in some embodiments, the volume estimation system 404 can include a database 414. As is described in greater detail below, the volume estimation system 404 can utilize the database 414 to store initial impedance images, enhanced impedance images, and/or fluid volume estimations and values.

In some embodiments, the volume estimation system 404 further includes a client application 412 installed thereon. In one or more embodiments, the client application 412 can be associated with the volume estimation system 404. For example, the client application 412 allows the user 410, the EIT system 402, and/or the additional systems 408 to directly or indirectly interface with the volume estimation system 404, the EIT system 402, and/or the additional systems 408. For example, the client application 412 can include a web browsing application and/or a specific volume estimation application.

The additional systems 408 may include additional systems that may interface with the volume estimation system 404 and/or provide data to the volume estimation system 404. For example, in some embodiments, the additional systems 408 may include computed tomography system (e.g., a CT scanner), an x-ray system, a magnetic resonance imaging system, an echocardiogram device, or any other device for producing images and/or data representing internal portions of a domain (e.g., a patient), model (e.g., prior model), and/or simulation.

The volume estimation system 404 may represent various types of computing devices with which users (e.g., an administrator) may interact. For example, the volume estimation system 404 may be a mobile device (e.g., a cell phone, a smartphone, a PDA, a tablet, a laptop, a watch, a wearable device, etc.). In some embodiments, however, the volume estimation system 404 can be a non-mobile device (e.g., a desktop or server). Additional details with respect to volume estimation system 404 are discussed below with respect to FIG. 20.

Figure 5A:
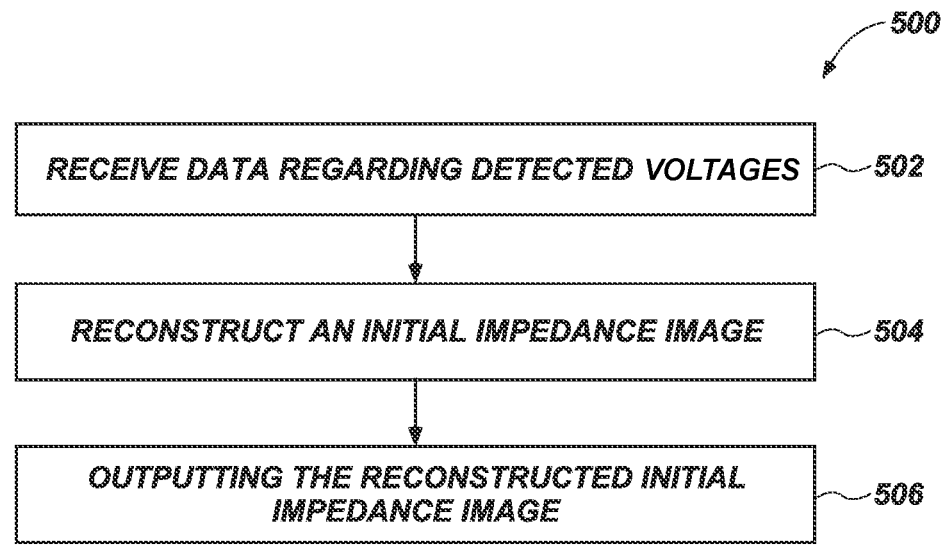
FIG. 5A is a flowchart of a method of reconstructing an EIT image according to one or more embodiments of the present disclosure.
Figure 5B:
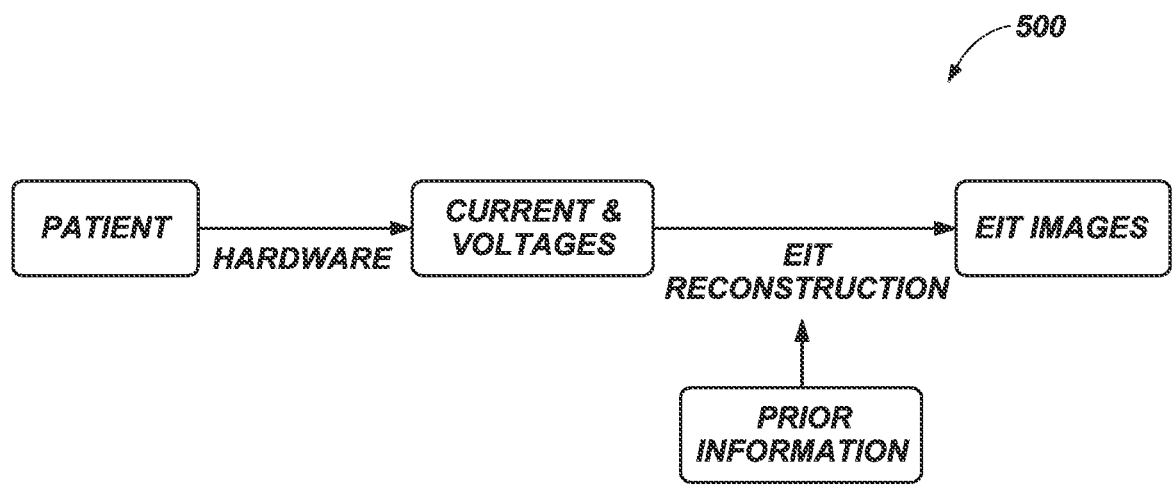
FIG. 5B is a schematic block diagram of the method of FIG. 5A.

FIG. 5A is a flowchart of a method 500 of reconstructing an EIT image according to one or more embodiments of the present disclosure. FIG. 5B is a schematic block diagram of the method 500 of FIG. 5A. Referring to FIGS. 5A and 5B together, the method 500 may be performed by one or more of the volume estimation system 404, the EIT system 402, the additional systems 408, or any combination thereof.

In some embodiments, the method 500 includes receiving data regarding voltages (e.g., electric potentials) detected by electrodes of an EIT system (e.g., the EIT system 402)

during an EIT imaging procedure, as shown in act 502 of FIG. 5A. For instance, receiving data regarding the voltages detected by the electrodes of the EIT system 402 may include data regarding voltages detected after applying voltages and/or currents to a domain (e.g., patient) via any of the procedures described above in regard to FIGS. 1-3. In some embodiments, the method 500 may include the volume estimation system 404 receiving the data regarding the detected voltages from the EIT system 402. In one or more embodiments, the volume estimation system 404 may detect/measure the voltages directly by passing one or more portions of the EIT system 402.

In some embodiments, the method 500 may include utilizing the received data regarding the detected voltages to reconstruct an initial impedance image, as shown in act 504. In some embodiments, reconstructing the initial impedance image may include reconstructing one or more of an initial absolute impedance image or an initial difference impedance image. For example, one or more of the volume estimation system 404, the EIT system 402, the additional systems 408, or any combination thereof may reconstruct the initial impedance image.

As is known in the art, an absolute impedance image represents electrical properties (e.g., represents electrical properties via pixels, voxels, etc.) throughout a respective two-dimensional or three-dimension section of the domain (e.g., a patient) at a given time, and a difference impedance image represents changes in electrical properties throughout a two-dimensional or three-dimension section of the domain (e.g., a patient) from a reference state. For example, each pixel and/or voxel may be associated with and/or may represent an impedance of a corresponding portion of the region of interest. As used herein, an "initial impedance" image may refer to one or more of an absolute impedance image or a different impedance image.

Image reconstruction is formulated as an inverse problem (referred to hereinafter as "the reconstruction problem") which calculates an estimate of a distribution of internal properties (e.g., impedance properties), which best represent the measured electrical potentials. As is discussed in greater detail below, reconstructing the initial impedance image (i.e., act 504) may include utilizing iterative algorithms that attempt to minimize an objective function (e.g., a cost function) and utilizing regularization techniques to reduce error propagation, improve stability of the iterations (e.g., iterative algorithms), and/or conditions of the reconstruction problem. Also, in some embodiments, reconstructing the initial absolute impedance image (i.e., act 504) may include utilizing a Bayesian technique, in which a priori information may be used as a regularization of the problem and the maximum a posteriori of a conditional probability density function may be used as an objective function.

As noted above, in some embodiments, reconstructing an initial impedance image may include reconstructing an initial impedance image via one or more iterative processes. For instance, reconstructing the initial impedance image may include reconstructing an initial impedance image via one or more methods such as, for example, a Gauss-Newton reconstruction approach, a Noser approach, a Simulated Annealing approach, a Kalman Filter approach, a Level Set approach, a Markov chain Monte Carlo approach, a Blackbox approach, a Back Projection approach, a Total Variation approach, or a Non-Linear Programming approach. In additional embodiments, reconstructing the initial impedance image may include reconstructing an initial impedance image via a Landweber iteration approach.

In some embodiments, reconstructing the initial impedance image may include reconstructing the initial impedance image via one or more direct methods. In other words, reconstructing the initial impedance image may include reconstructing the initial impedance image without input from external data sources (e.g., prior information). For instance, reconstructing the initial impedance image may include reconstructing an initial impedance image via one or more methods such as, for example, a direct D-bar reconstruction algorithm, a Calderon's method, or an algebraic reconstruction technique. In additional embodiments, as described below, reconstructing the initial impedance image may include reconstructing the initial impedance image based at least partially on external data sources (e.g., prior information).

In some embodiments, reconstructing the initial impedance image may include reconstructing the initial absolute impedance image using one or more regularization methods. For instance, reconstructing the initial impedance image may include using one or more regularization methods to reconstruct the initial impedance image such as, for example, a Generalized Tikhonov Regularization (e.g., a Gaussian high-pass filter), utilizing prior information (e.g., taking into account a probability density function, as described below) and/or regularization utilizing a total variation (TV) functional.

As noted above, in one or more embodiments, reconstructing the initial impedance image may further include reconstructing the initial impedance image based at least partially on prior information (i.e., one or more priors). As used herein, "prior information" and "priors" may refer to data (e.g., one or more images or scans and/or one or more images of other imaging modalities (e.g., CT-scans) of a population and/or the patient) external to the data provided by the EIT data that may inform (e.g., provide additional information to) an image generation process (e.g., the reconstruction process). For instance, the prior information may include one or more computerized tomography (CT) scans that may be utilized to add prior information into the EIT reconstruction algorithms. In particular, the CT scans can provide anatomy-based and/or physiological-based priors, and the initial impedance image may be reconstructed based at least partially on the information the anatomy-based priors provide. For example, the CT scans (e.g., the priors) may be used to build a regularization term for the regularization methods described above. Additionally, the prior information may be utilized to build a regularization term and determine an approximation error. In some embodiments, the prior information may include images from other imaging modalities and/or data from other sensors (e.g., pneumotachograph, plethysmograph, etc.).

In some embodiments, the prior information may be specific to the domain (e.g., a patient) for which an initial impedance image is being reconstructed. For example, the prior information may include CT-scans (or other data) of the domain (e.g., CT-scans at or proximate where EIT data is measure (e.g., at or proximate the electrode belt of the EIT system)). In other embodiments, the prior information may include CT-scans (or other data) of one or more anatomy or physiological models (e.g., physical models). In further embodiments, the prior information may include data from one or more digital models and/or simulations. In some embodiments, prior information may be selected and/or obtained based at least partially on a class of the domain (e.g., an age, gender, race, weight, etc.). For example, in some embodiments, prior information may be selected and/ or obtained based at least partially on anthropometric measures. In additional embodiments, the prior information may be selected and/or obtained based at least partially on a type of diagnostic procedure (e.g., a pneumothorax, an FRC, a tidal volume, and/or a cellularity on pleural fusion diagnostic procedure) to be performed with eventual generated data (e.g., a fluid estimation values). In further embodiments, the prior information may be selected and/or obtained based at least partially on a type of volumetric image to be generated (e.g., an air, a blood, and/or a water volumetric image).

In some embodiments utilizing prior information in reconstructing the initial impedance image may include using the prior information (e.g., CT scans) as anatomical atlases in reconstructing the initial impedance image. In such embodiments, the probability density functions of a resistivity distribution in the region of the body, $\pi(\rho_{sw})$ may be represented as the following Gaussian distribution:

$$\pi(\rho_{sw}) \propto e^{-\frac{1}{2}(\rho-\bar{\rho}_{sw})^T \Gamma_{sw}^{-1}(\rho-\bar{\rho}_{sw})} \quad (1)$$

In the above equation, the mean ($\bar{\rho}_{sw}$) and covariance matrix ($\Gamma_{sw}$) of the probability density function may be utilized to estimate the initial absolute impedance images. As noted above, the prior information is the regularization term (second term (i.e., the second line of the above equation)) of the following equation (2):

$$F_2(\rho) = \frac{1}{2}(\phi_m^q - \phi_e^q(\rho))^T (\phi_m^q - \phi_m^q(\rho)) + \gamma^2 (\rho - \bar{\rho}_{sw})^T \Gamma_{sw}^{-1}(\rho-\bar{\rho}_{sw}) + \lambda^2 (\rho-\bar{\rho}_{sw})^T F^T F (\rho-\bar{\rho}_{sw}) \quad (2)$$

where F is a Gaussian high pass filter, $\Gamma_{sw}$ is a covariance matrix of a statistical prior, interpolated to a Finite Element Mesh (FEM), $\bar{\rho}_{sw}$ is an expected vector of resistivities of the statistical prior, which is also interpolated to the FEM mesh, and γ is the regularization parameter for the prior information. A third term (i.e., the third line of the above equation) may not be necessary if the prior information is informative enough in all the directions (e.g., x, y, and z directions) in which the first term (i.e., the first line of the above equation) may not be informative.

In equation (2), the first term (i.e., the first line) originates from a likelihood, the second term (i.e., the second line) is the prior information, and the third term (i.e., the third line) is a smoothness prior. Equation (2) penalizes spatial high frequency image components of the difference between candidate ρ and the statistically expected ($\bar{\rho}_{sw}$). As a non-limiting example, reconstructing the initial impedance image utilizing prior information may include reconstructing an initial impedance image via any of the manners described in T. de Castro Martins et al., "A review of electrical impedance tomography in lung applications: Theory and algorithms for absolute images," Annual Reviews in Control, Volume 48, 2019, pages 442-471, the disclosure of which is incorporated in its entirety by reference herein.

Upon reconstructing the initial impedance image, the method 500 may include generating and/or outputting the reconstructed initial impedance image, as shown in act 506 of FIG. 5. For example, outputting the reconstructed initial impedance image may include generating a data package including/representing the initial impedance image and/or storing the initial impedance image in a database (e.g., database 414). In some embodiments, the reconstructed initial impedance image may be represented by pixels (e.g., two-dimensional images), by voxels (three-dimensional images), by elements of the FEM, or any combination of the foregoing elements.

Referring to acts 502-506 together, in some embodiments, the method 500 may include generating a plurality of initial impedance images. For example, the method 500 may include generating a plurality of initial impedance images along a plurality of planes (e.g., slices) or sections along an axial length of the domain (e.g., patient).

Referring still to FIGS. 5A and 5B, the initial impedance image and the electrical properties represented therein may be underestimated in one or more regions (e.g., underestimated due to the linearity of, for example, the Gauss-Newton reconstruction method), may have relatively low spatial resolution, may include image artifacts, etc. Therefore, an enhancement (e.g., correction) of the initial impedance image may be desirable to improve a diagnostic quality of the initial impedance image (e.g., an ability to perform a diagnoses from the initial impedance image or resulting volume estimations determined from the initial impedance image).

Figure 6:
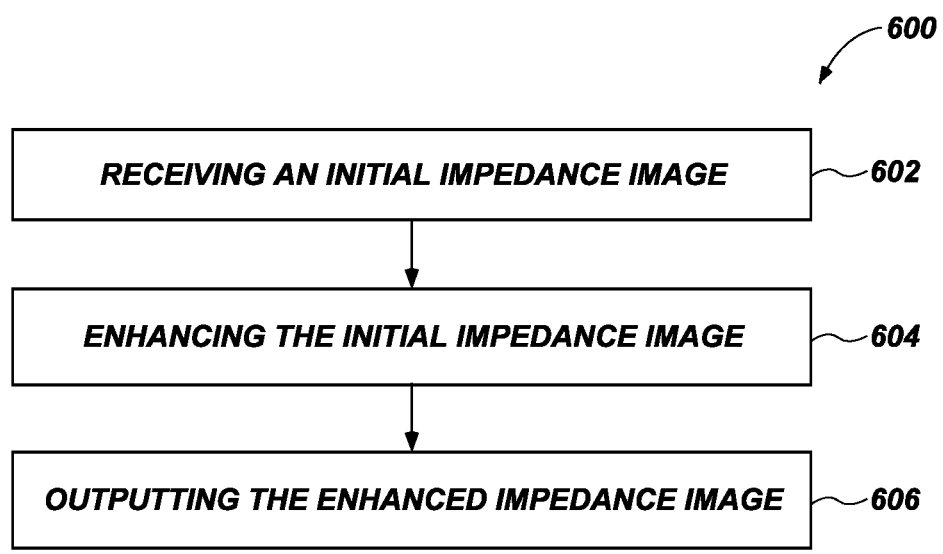
FIG. 6 is a flowchart of a method of enhancing an initial impedance image according to one or more embodiments of the present disclosure.

FIG. 6 is a flowchart of a method 600 of enhancing an initial impedance image (e.g., the reconstructed initial impedance image described above in regard to FIGS. 5A and 5B) according to one or more embodiments of the present disclosure.

In one or more embodiments, the method 600 may include receiving an initial impedance image, as shown in act 602 of FIG. 6. In some embodiments, the method 600 may include receiving the initial impedance image from an EIT system (e.g., the EIT system 402). In one or more embodiments, the method 600 may include the volume estimation system 404 receiving the initial impedance image from the EIT system 402. In additional embodiments, the method 600 may include receiving the initial impedance image from an additional system (e.g., additional system 408), querying a database (e.g., database 414) to retrieve the initial impedance image, or receiving the initial impedance image from an external source. As noted above, the initial impedance image may be represented by pixels (e.g., two-dimensional images), by voxels (three-dimensional images), by elements of the FEM, or any combination thereof.

Responsive to receiving and/or retrieving the initial impedance image, the method 600 may further include directly enhancing (e.g., correcting) the initial impedance image, as shown in act 604 of FIG. 6. In particular, the method 600 may include enhancing the initial impedance image without additional information input (e.g., prior information).

In one or more embodiments, directly enhancing (e.g., correcting) the initial impedance image may include enhancing the initial impedance image through a D-bar method. For example, enhancing the initial impedance image may include enhancing the initial impedance image through any of the manners described in Melody Dodd et al., "A Real-time D-bar Algorithm for 2-D Electrical Impedance," Inverse Probl Imaging (Springfield). 2014 Nov. 1; 8(4): 1013-1031. DOI: 10.3934/ipi.2014.8.1013, the disclosure of which is incorporated in its entirety by reference herein. Furthermore, enhancing the initial impedance image may include enhancing the initial impedance image through any conventional D-bar methods.

Enhancing the initial impedance image via a D-bar method (or any other reconstruction method) may estimate true or relatively close values of the electrical properties represented by, for example, the pixels of the initial impedance image of a region of interest of the domain (e.g., patient). Therefore, enhancing the initial impedance image via a D-bar method may correct electrical properties represented in the initial impedance image of the region of interest of the domain (e.g., patient). As a non-limiting example, enhancing the initial impedance image via D-bar method may include identifying organs (e.g., lungs, heart, kidneys) and bones from the initial impedance image and then adjusting the associated electrical properties represented in the areas of the initial impedance identified as organs and/or bones based on the identified organs and/or bones via the D-bar method.

Upon enhancing the initial impedance image, the method 600 may include outputting an enhanced impedance image, as shown in act 606 of FIG. 6. For example, the volume estimation system 404 may output the enhanced impedance image. In some embodiments, outputting the enhanced impedance image may include outputting an enhanced absolute impedance image. In additional embodiments, outputting the enhanced impedance image may include outputting an enhanced difference impedance image. In one or more embodiments, outputting the enhanced impedance image may include may include generating a data package including the enhanced impedance image and/or storing the enhanced impedance image in a database (e.g., database 414). In some embodiments, the enhanced impedance image may be represented by pixels (e.g., two-dimensional images), by voxels (three-dimensional images), by elements of a FEM, or any combination thereof.

Figure 7A:
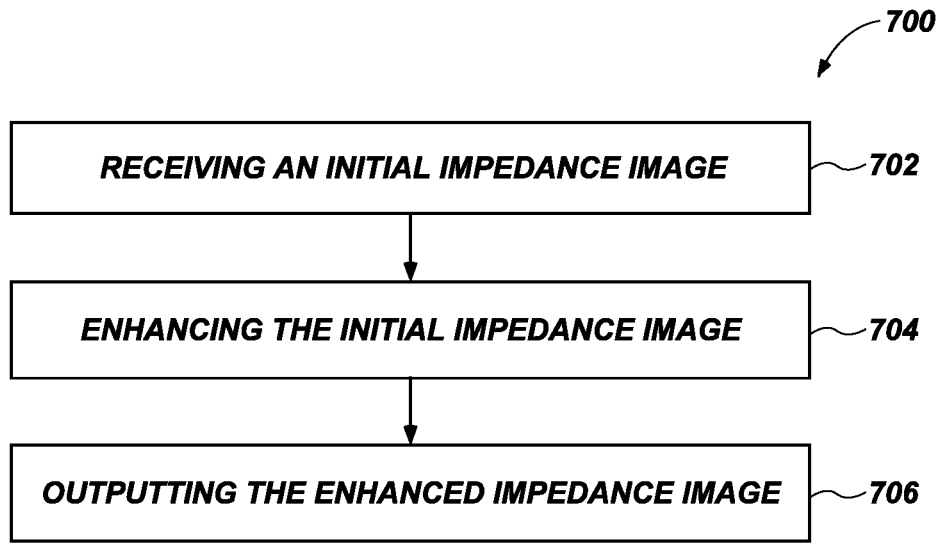
FIG. 7A is a flowchart of a method of enhancing an initial impedance image according to one or more additional embodiments of the present disclosure.
Figure 7B:
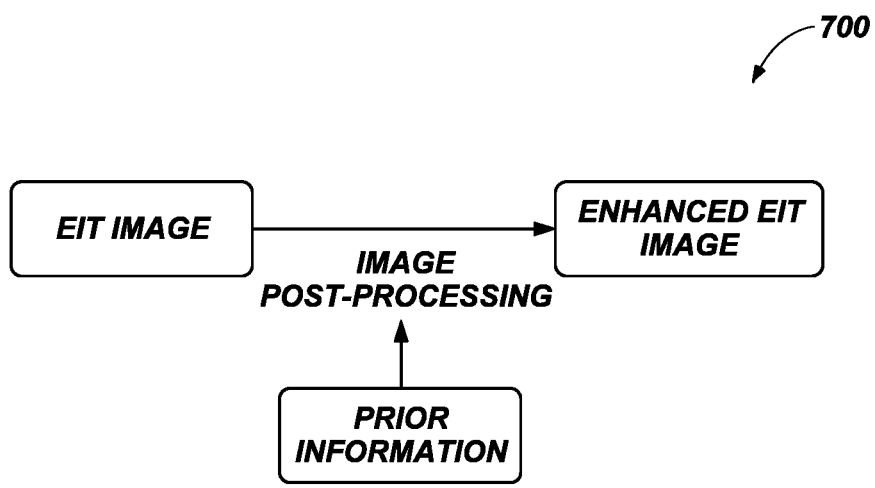
FIG. 7B is a schematic block diagram of the method of FIG. 7A.

FIG. 7A is a flowchart of a method 700 of enhancing an initial impedance image (e.g., the reconstructed initial impedance described above in regard to FIGS. 5A and 5B) according to one or more additional embodiments of the present disclosure. FIG. 7B is a schematic block diagram of the method 700 of FIG. 7A. The method 700 may include utilizing prior information to enhance the initial impedance image.

Figure 8:
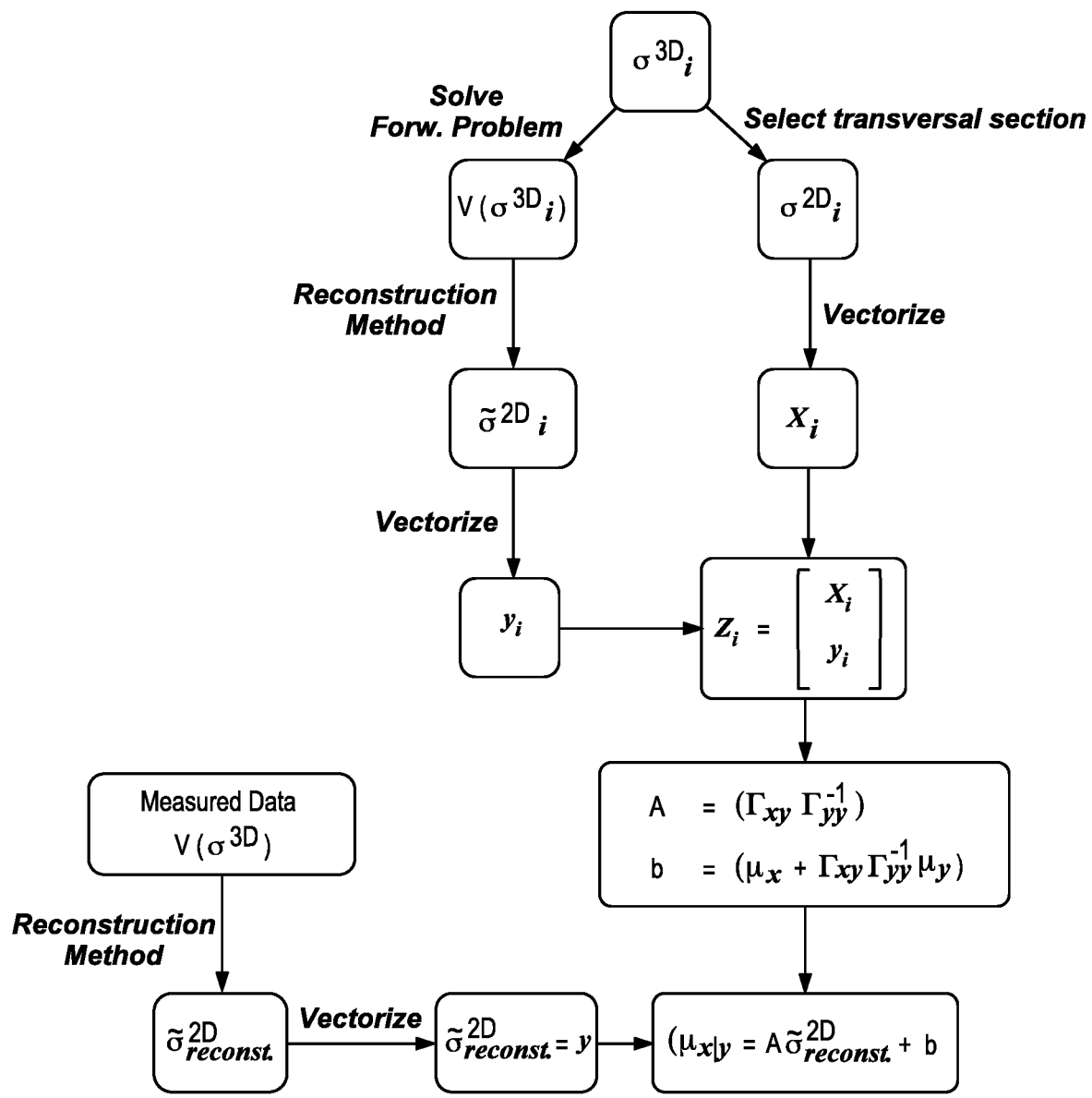
FIG. 8 is a schematic block diagram that depicts portions of a Schur complement approach of enhancing an impedance image utilizing prior information.

In one or more additional embodiments, enhancing (e.g., correcting) the initial impedance image may include enhancing the initial impedance image through a Schur complement approach. In particular, the Schur complement approach may utilize Schur complement properties to introduce statistical prior information into a D-bar method and may provide a significant improvement in spatial resolution of the initial impedance image. In other embodiments, the Schur complement may be used as a direct enhancement method as described above in regard to FIG. 6. FIG. 8 is a schematic block diagram that depicts portions of the Schur complement approach utilizing prior information (e.g., information from prior models).

The prior information and/or prior models may include segmented tomographic images of a portion of a body (e.g., a thorax) of the domain (e.g., patient), and the electrical property distribution of the tissues may be utilized to perform numerical phantoms (described in greater detail below). For example, a CT-scan may be segmented into different tissues (e.g., bones, aerated lungs, atelectasis, heart, and/or muscles) according to the respective tissue's characteristics in regard to grey levels. As a result, the correct electrical property distributions within the initial impedance image may be generated (e.g., built, adjusted, and/or corrected) using the electrical property distribution of the tissues (which may have been measured in vivo).

Referring to FIGS. 7A-8 together, in some embodiments, the method may include introducing prior information based on Schur Complement properties. For example, the method may include applying a correction (e.g., post processing) to the initial impedance image by maximizing a conditional probability density function of an image that is consistent with the prior information, considering the initial impedance image.

Based on Schur complement properties, a conditional mean $\mu_{x|y}$ may be determined by the following equation (3)

$$\mu_{x|y} = Ay + b \qquad (3)$$

From one or more (e.g., a set of) prior samples $\sigma_i^{3D}$, an estimate of the probability distribution of a population $\pi(x)$ may be determined. The one or more prior samples $\sigma^{3D}$ may be determined by segmenting tomography images/scans, and electrical properties may be established for each region identified in a resulting segmentation.

For each resulting electrical property distribution $\sigma_i^{3D}$ (e.g., segmented prior samples), two images may be determined (e.g., computed). A first determined image ($\sigma_i^{2D}$) may represent an electrical property distribution of $\sigma_i^{3D}$, where the electrode belt is oriented on the thorax of the domain. To obtain the first image $\sigma_i^{2D}$, a Gaussian interpolation may be applied to $\sigma^{3D}$ and may account for a specific height and thickness of $\sigma_i^{3D}$. A second determined image ($\tilde{\sigma}_i^{2D}$) may represent a reconstructed image of $\sigma_i^{2D}$. To obtain the second image $\tilde{\sigma}_i^{2D}$, first, a vector $V(\sigma_i^{3D})$, which represents the forward problem of the electrical property distribution $\sigma_i^{3D}$, may be determined (e.g., calculated), and second, the second image $\tilde{\sigma}_i^{2D}$ may be estimated by a reconstruction method using the determined vector $V(\sigma_i^{3D})$ (i.e., the determined voltages).

The two resulting images $\sigma_i^{2D}$ and $\tilde{\sigma}_i^{2D}$ may be converted into vectors and may be represented by $x_i$ and $y_i$, respectively. Additionally, a new vector $z_i$ may be generated by concatenating $x_i$ and $y_i$:

$$z_i = \begin{bmatrix} x_i \\ y_i \end{bmatrix} \qquad (3)$$

Additionally, by determining estimates of $x_i$ and $y_i$ for multiple prior samples $\sigma_i^{3D}$, an expected value $\mu_z$ and the covariance $\Gamma_z$ of the z process may be determined. From the expected value $\mu_z$ and the covariance $\Gamma_z$ of the z process, a statistics and relation between a set of images $x_i$ and $y_i$ may be obtained.

$$\mu_z = \begin{bmatrix} \mu_x \\ \mu_y \end{bmatrix} \qquad (4)$$

$$\Gamma_z = \begin{bmatrix} \Gamma_{xx} & \Gamma_{xy} \\ \Gamma_{yx} & \Gamma_{yy} \end{bmatrix} \qquad (5)$$

where $\mu_x$ and $\mu_y$ are the expected values of the $x_i$ and $y_i$ set of images, $\Gamma_{xx}$ and $\Gamma_{yy}$ are the covariance matrices of each set of images, and $\Gamma_{xy}$ and $\Gamma_{yx}$ are their cross-covariance matrices.

An estimate of the vector $x_i$ may be determined from $y_i$ by using the prior statistics and relation between the set of images $x_i$ and $y_i$.

$$\mu_{x|y} = \mu_x + \Gamma_{xy}\Gamma_{yy}^{-1}(y - \mu_y) \qquad (6)$$

By reordering equation (6), a first-order correction for the initial impedance image ($\sigma_{reconst}^{2D}$) from the reconstruction method may be determined. The correction may consider the prior distribution of a population and the forward problem model.

$$\mu_{x|y} = \Gamma_{xy}\Gamma_{yy}^{-1}y + (\mu_x - \Gamma_{xy}\Gamma_{yy}^{-1}\mu_y) \qquad (7)$$

$$\mu_{x|y} = Ay + b \qquad (8)$$

In summary, by using the Schur complement approach described herein, regional averages and conditional covariances may be determined, that the regional averages and conditional covariances may be utilized to determine (e.g., calculate) corrected impedances of the initial impedance image. Accordingly, the initial impedance image may be enhanced utilizing the Schur complement approach described above. Additionally, the initial impedance image may be enhanced using any combination of an alternative reconstruction method enhancement (e.g., D-bar method) and Schur complements approach described above.

In additional embodiments, as noted above, the initial impedance image may be enhanced via numerical phantom simulations. In particular CT-scans may be segmented and transformed into electrical property distributions according to the electrical property distribution of each segmented tissue. Subsequently, numerical phantoms may be generated for these electrical property distributions, and reference reconstruction images may be determined based at least partially on these electrical property distributions.

Furthermore, based on a comparison between the electrical property distributions represented in the initial impedance image and the reference reconstructed images, a relationship function (e.g., linear function or non-linear function) may be determined and utilized to adjust the electrical properties within a region of interest of the initial impedance image. In some instances, various machine learning models may be utilized within the process of enhancing the initial impedance images. For instance, enhancing the initial impedance image may include machine learning and/or deep learning techniques that include providing training corpora to a matching learning algorithm or neural network to train a machine to aid or perform enhancing the initial impedance image or portions of the initial impedance image. In some embodiments, the volume estimation system 404 may enhance at least a portion of the initial impedance image one or more of regression models (e.g., a set of statistical processes for estimating the relationships among variables), classification models, and/or phenomena models. Additionally, the machine-learning models may include a quadratic regression analysis, a logistic regression analysis, a support vector machine, a Gaussian process regression, ensemble models, or any other regression analysis. Furthermore, in yet further embodiments, the machine-learning models may include decision tree learning, regression trees, boosted trees, gradient boosted tree, multilayer perceptron, one-vs-rest, Naïve Bayes, k-nearest neighbor, association rule learning, a neural network, deep learning, pattern recognition, or any other type of machine-learning.

In some embodiments, enhancing the impedance image may include any combination of the methods described above in regard to FIGS. 6-8. For example, one or more portions (e.g., pixels and/or regions) of the initial impedance image may be enhanced via a first method and one or more other portions (e.g., pixels and/or regions) of the initial impedance image may be enhanced via a second, different method.

Upon enhancing the initial impedance image, the method 700 may include outputting an enhanced impedance image, as shown in act 706 of FIG. 7A. For example, the volume estimation system 404 may output the enhanced impedance image. In some embodiments, outputting the enhanced impedance image may include outputting an enhanced absolute impedance image. In additional embodiments, outputting the enhanced impedance image may include outputting an enhanced difference impedance image. In one or more embodiments, outputting the enhanced impedance image may include generating a data package including/representing the enhanced impedance image and/or storing the enhanced impedance image in a database (e.g., database 414). In some embodiments, the enhanced impedance image may be represented by pixels (e.g., two-dimensional images), by voxels (three-dimensional images), by elements of a FEM, or any combination thereof.

Figure 9A:
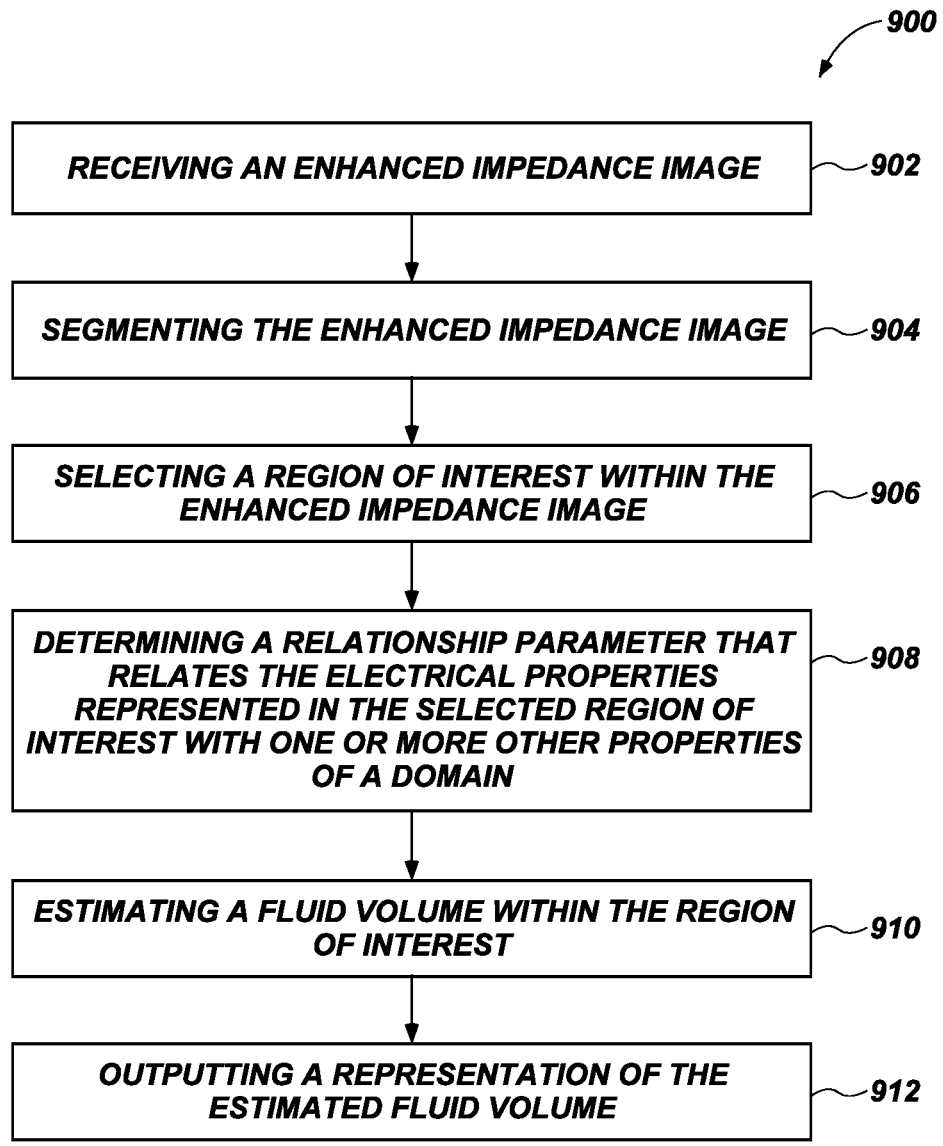
FIG. 9A is a flowchart of a method of determining a fluid volume estimation within a region of a body.
Figure 9B:
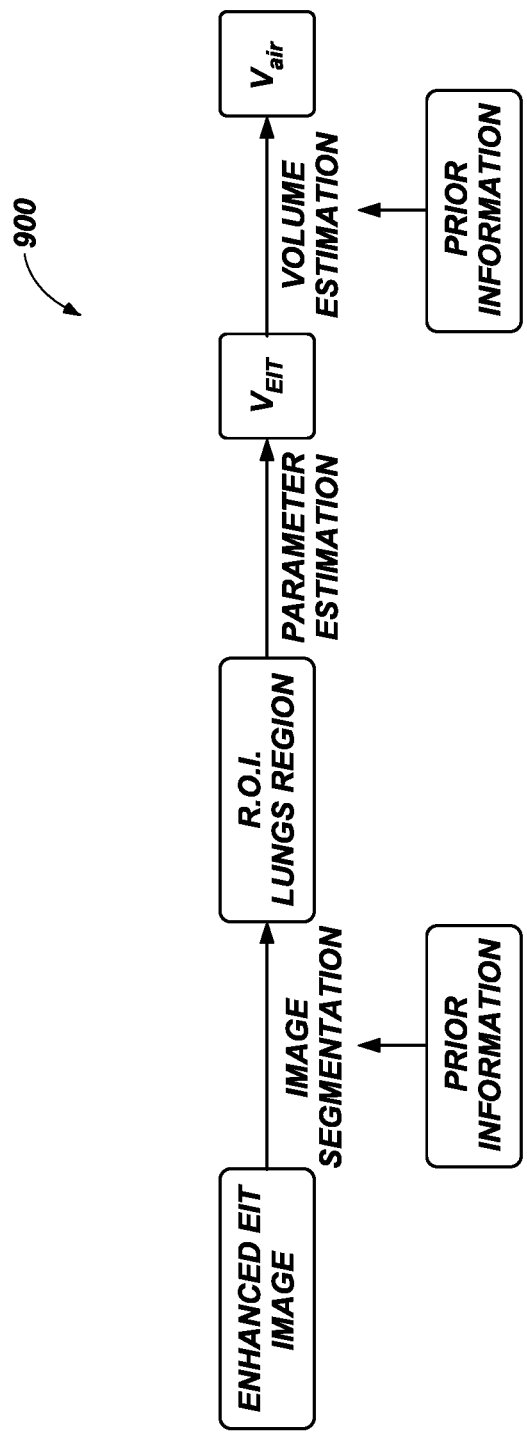
FIG. 9B is a schematic block diagram showing the method of FIG. 9A.

FIG. 9A is a flowchart of a method 900 of determining a fluid volume estimation within a region of a body. FIG. 9B is a schematic block diagram showing the method 900 of FIG. 9A.

Referring to FIGS. 9A and 9B together, the method 900 may include receiving an enhanced impedance image, as shown in act 902 of FIG. 9A. For example, the method 900 may include receiving any of the enhanced (e.g., corrected) impedance images discussed above in regard to FIGS. 6-8. In particular, the volume estimation system 404 may receive the enhanced impedance image. As noted above, in some embodiments, the enhanced impedance image may include an enhanced absolute impedance image or an enhanced difference impedance image. In some embodiments, receiving an enhanced impedance image may include receiving a data package representing the enhanced impedance image and/or querying the database 414 to retrieve the enhanced impedance image.

Responsive to receiving the enhanced impedance image, the method 900 may include segmenting the enhanced impedance image, as shown in act 904 of FIG. 9A. For example, the method 900 may include applying one or more segmentation processes to the enhanced impedance image. For instance, the volume estimation system 404 may partition the enhanced impedance image into multiple segments (e.g., sets of pixel and/or image object).

Segmenting the enhanced impedance image may include locating objects (e.g., lungs, heart, kidneys, bones, and/or other organs) and boundaries (e.g., lines, curves, etc.) within the images. For instance, the result of the image segmentation may include a set of segments that collectively cover the entire enhanced image and/or a set of contours extracted from the image (e.g., edge detection). Segmenting the enhanced impedance image may include applying any conventional image segmentation process to the enhanced impedance images.

In some embodiments, the image segmentation process may be informed by prior information. For example, in some embodiments, segmenting the enhanced impedance image may include utilizing one or more priors (e.g., CT-scans) that have also been segmented to identify objects (e.g., organs and/or bones) and/or regions of interest within the enhanced impedance image. As another non-limiting example, segmenting the enhanced impedance image may include utilizing a mean contour of a segmented object (e.g., organ) within the one or more priors (e.g., CT-scans) to select a region of interest of as a region of the segmented object.

Upon segmenting the enhanced impedance image, the method 900 may include selecting a region of interest within the enhanced impedance image, as shown in act 906 of FIG. 9A. For instance, the method 900 may include selecting a region of interest within the enhanced impedance image via any of the manners described above in regard to act 904 of FIG. 9A (e.g., utilizing prior information). In some embodiments, selecting a region of interest within the enhanced impedance image may include selecting a region representing one or more organs or one or more bones or any other part of a body of a patient. For example, selecting a region of interest within the enhanced impedance image may include selecting a region representing a lungs region of the patient. In one or more embodiments, selecting a region of interest within the enhanced impedance image may include selecting a region representing a portion of the body to be analyzed (e.g., a portion of the body where a measurement of a fluid volume is desired).

The selected region of interest of the enhanced impedance image may provide (e.g., connote, represent, define) an electrical property distribution through the selected region via values represented by the pixels, voxels, and/or FEM elements of the enhanced impedance image.

Responsive to selecting the region of interest of the enhanced impedance image, the method 900 may include determining a relationship parameter ($V_{EIT}$) that relates the electrical properties (e.g., impedances) represented in the selected region of interest with one or more other properties of the patient within the region of interest, as shown in act 908 of FIG. 9A. For example, the relationship parameter ($V_{EIT}$) may include a linear or nonlinear function that relates fluid content and electrical properties of the region of interest. In some embodiments, the one or more other properties may include air content (e.g., a total volume of air and/or air volume indicated by one or more pixels, voxels, and/or elements of a FEM) in the region, blood content in the region, tissue content in the region.

In some embodiments, the relationship parameter ($V_{EIT}$) may be determined from the electrical properties (e.g., impedances) represented in the selected region of interest. For instance, the relationship parameter ($V_{EIT}$) may be determined via a weighted sum model. For example, the relationship parameter ($V_{EIT}$) may be determined via the following weighted sum:

$$V_{EIT} = \Sigma(\rho_i v_i) \quad (17)$$

where $\rho_i$ is an electrical resistivity distribution represented in the enhanced impedance image of the region of interest, and $v_i$ is a tetrahedron volume of a Finite Element Mesh representation of the region of interest. Alternatively, $v_i$ is pixel area and/or voxel volume represented in the enhanced impedance image. In view of the foregoing, the relationship parameter ($V_{EIT}$) may be unique to the selected region of interest. In some embodiments, a relationship parameter may be determined for each pixel, voxel, and/or FEM element of the enhanced impedance image.

Upon determining the relationship parameter ($V_{EIT}$), the method 900 may include estimating a fluid volume ($V_{fluid}$ (e.g., $V_{air}$)) within the region of interest, as shown in act 910 of FIG. 9A. For example, the volume estimation system 404 may estimate a fluid volume within the region of interest. An example method of estimating the fluid volume is described below.

A variation of the electrical resistivity distribution represented in the region of interest in the enhanced impedance image may correlate substantially linearly to a fluid content variation in the region of interest of the domain (e.g., the selected region of interest). Accordingly, based on the determined relationship parameter ($V_{EIT}$), estimating the fluid volume ($V_{fluid}$) may include estimating the fluid volume ($V_{fluid}$) via a linear model. For example, estimating the fluid volume ($V_{fluid}$) may include estimating the fluid volume ($V_{fluid}$) via the following model:

$$V_{fluid} = a \cdot V_{EIT} + b \quad (18)$$

Variables a and b may be calculated (e.g., estimated) by relating an air content estimated from prior information (e.g., CT-scans), as described above in regard to act 908 of FIG. 9A, and the relationship parameter ($V_{EIT}$). Estimating variables a and b is described in greater detail below in regard to FIGS. 19A-19C and Tables 3-6.

In some embodiments, estimating the fluid volume ($V_{fluid}$) may be informed by prior information, as shown in FIG. 9B. For example, in some embodiments, estimating the fluid volume ($V_{fluid}$) include utilizing one or more priors (e.g., CT-scans) to determine a fluid content by correlating the Hounsfield unit scale and a fluid volume in a tissue of the region of interest (e.g., the tissue of lungs). As is known in the art, the Hounsfield unit scale is a linear transformation of an original linear attenuation coefficient measurement into one in which a radiodensity of water (e.g., distilled water) at standard pressure and temperature (STP) is defined as zero Hounsfield units (HU), while a radiodensity of air at STP is defined as −1000 HU. In a voxel with an average linear attenuation coefficient $\mu$, the corresponding HU value is therefore given by:

$$HU = 1000 \times \frac{\mu - \mu_{water}}{\mu_{water} - \mu_{air}} \quad (19)$$

where $\mu_{water}$ and $\mu_{air}$ are respectively the linear attenuation coefficients of water and air. In view of the foregoing, a change of one Hounsfield unit (HU) represents a change of 0.1% of the attenuation coefficient of water because the attenuation coefficient of air is about zero.

In view of the foregoing, fluid content (e.g., air content) indicated by the prior information (e.g., CT-scan) can be correlated to the relationship parameter ($V_{EIT}$) determined from the enhanced impedance image. Furthermore, based on the correlation be between the fluid content indicated by the prior information and the relationship parameter ($V_{EIT}$), the relationship parameter ($V_{EIT}$) may be refined, and the ultimate estimation of the fluid volume ($V_{fluid}$) may be refined. Additionally, in some embodiments, ($V_{EIT}$) and ($V_{fluid}$) may be correlated through, for example, linear or non-linear regression, machine learning, etc. Furthermore, in some embodiments, parameters a and b may be estimated by minimizing a mean square error between the priors and the ($V_{EIT}$) estimation. Additionally, ($V_{fluid}$) may be estimated by computing the maximum a posteriori of a conditional mean of ($V_{fluid}$) based at least partially on the enhanced impedance image.

As mentioned above, in some embodiments, estimating a fluid volume ($V_{fluid}$) may include estimating a volume of one or more of air, blood, water, and/or tissue. Responsive to estimating the fluid volume ($V_{fluid}$), the method 900 may include outputting a representation (e.g., value, image, etc.) of the estimated fluid volume ($V_{fluid}$), as shown in act 912 of FIG. 9A.

For example, the volume estimation system 404 may output the representation of the estimated fluid volume. In some embodiments, outputting the representation of the estimated fluid volume may include outputting an overall value representative of the estimated volume of a given fluid. In additional embodiments, outputting the representation of the estimated fluid volume may include outputting a volumetric image where each pixel, voxel, and/or element of a FEM represents a volume of a given fluid in the region associated with the pixel, voxel, and/or element. In some embodiments, outputting the representation of the estimated fluid volume may include outputting a representation of an absolute volume estimate. In additional embodiments, outputting the representation of the estimated fluid volume may include outputting a representation of a difference volume estimate. In one or more embodiments, outputting the representation of the estimated fluid volume may include generating a data package including the representation of the estimated fluid volume and/or storing the representation of the estimated fluid volume in a database (e.g., database 414).

The following description referring to FIGS. 10-19C describes a plurality of tests performed by the inventors for estimating fluid volumes within regions of a plurality of domains per the methods and processes described herein. The experiments included utilizing an EIT system to acquire voltage measurements. The electrodes for applying and detecting voltages were oriented in a zig-zag pattern around the domains. In the experiments, the domains included twelve piglets. The applied current patterns included sinusoidal, 10 mA, 125 kHz, and adjacent current patterns (skip-3).

Ten piglets were utilized to build anatomical atlases (mean and covariance) (e.g., to build prior information). The fluid estimation methods described herein were performed on the two remaining piglets, which were not included in the prior information.

Four CT-scans were taken of each of the ten piglets being utilized to build anatomical atlases. Each of the CT-scans were segmented and processed per the method described above in regard to FIGS. 7A and 7B. FIG. 10 shows example segmented and processed images.

Additionally, small perturbations simulating abnormal lungs were introduced to prior models (e.g., artificial models), CT-scans were taken of the prior models, and additional segmented images were artificially generated. The small perturbations were introduced by removing spherical objects from random positions in the modeled lungs and/or the modeled hearts. Table 1 shows the determined mean and standard deviations of the segmented tissues of FIG. 10 based on the measured electrical properties.

TABLE 1

| Tissue | Mean (ohm · m) | Std (ohm · m) |
|---|---|---|
| Lungs | 2.8 | 6.0 |
| Heart | 1.8 | 2.0 |
| Muscle | 2.9 | 2.0 |
| Bones | 29.5 | 1.0 |

FIG. 11 shows the generated prior information used to reconstruct impedance images of the ten piglets using a Gauss-Newton method. The anatomical atlases generated from the ten piglets and a high-pass Gaussian filter were used to regularize the inverse problem, and the conductivity distribution was estimated (e.g., reconstructed).

Figures 12A, 12B, 12C:
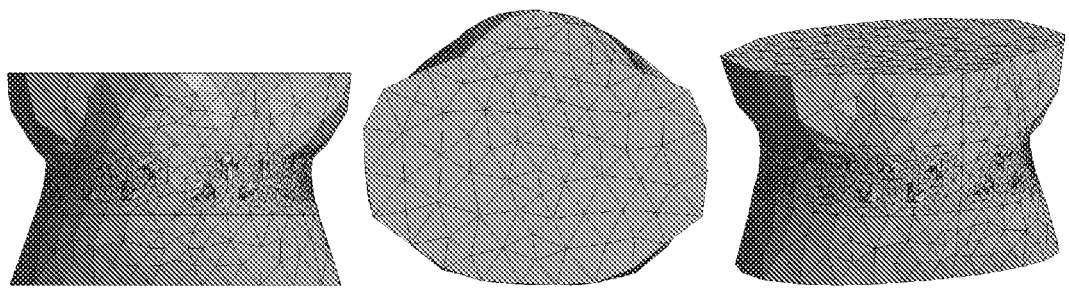
FIGS. 12A-12C show various views of a finite element mesh utilized to estimate electrical property distributions according to one or more embodiments of the present disclosure.
Figures 13A, 13B, 13C:
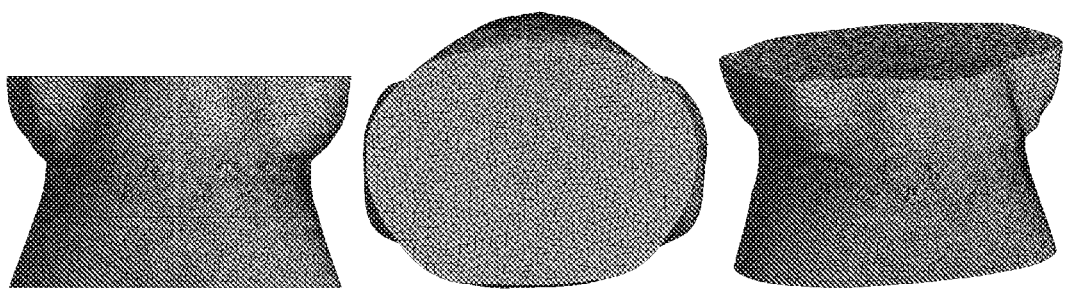
FIGS. 13A-13C show various views of a refined finite element mesh according to one or more embodiments of the present disclosure.
Figure 17A:
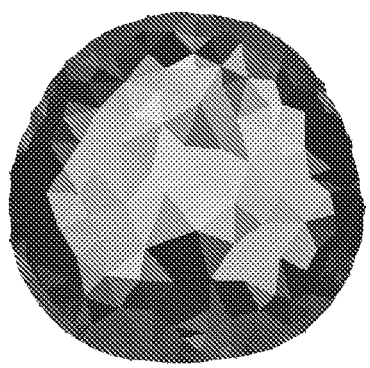
FIGS. 17A-17E show additional reconstructed initial impedance images reconstructed according to one or more embodiments of the present disclosure.
Figure 17B:
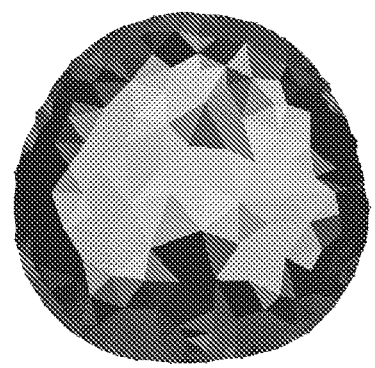
Figure 17C:
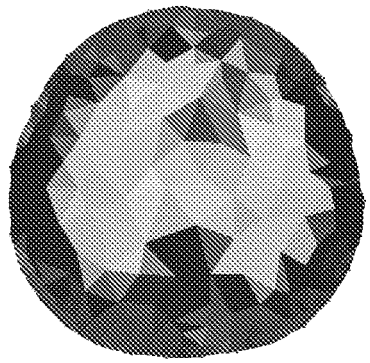
Figure 17D:
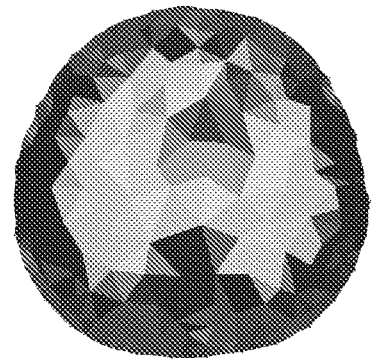
Figure 17E:
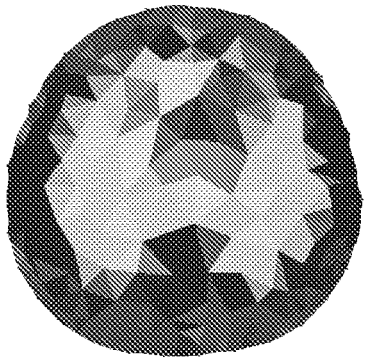
Figure 18A:
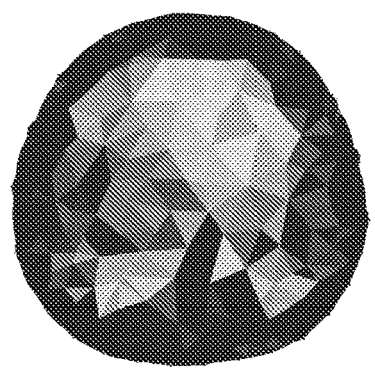
FIGS. 18A-18F show additional reconstructed initial impedance images reconstructed according to one or more embodiments of the present disclosure.
Figure 18B:
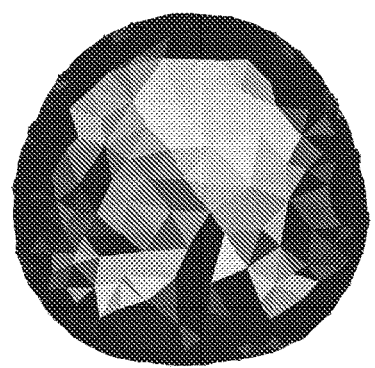
Figure 18C:
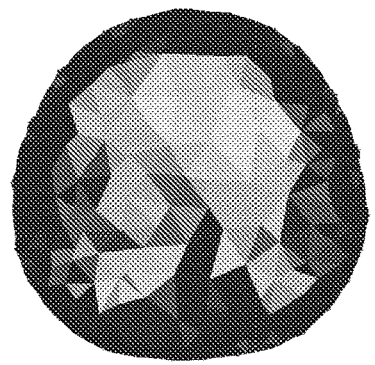
Figure 18D:
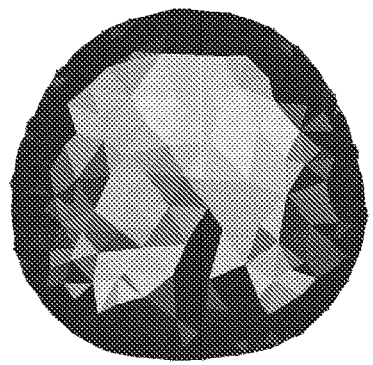
Figure 18E:
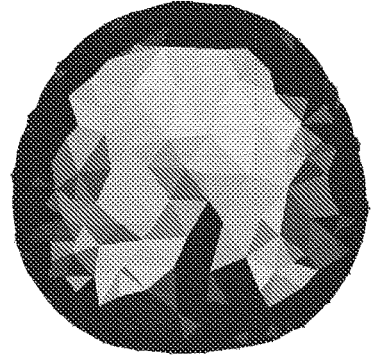
Figure 18F:
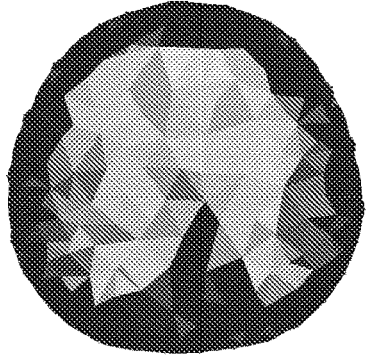

The initial impedance image (the conductivity electrical distribution) is estimated by using a finite element mesh, as depicted in FIGS. 12A-12C, and by utilizing the prior information to regularize the inverse problem. Additionally, an approximation error theory was applied using a refined finite element mesh, as depicted in FIGS. 13A-13C.

Additionally, voltage measurements were acquired for the two remaining piglets. FIG. 14 shows an example mean of the voltage measurements (e.g., mean of all electrode measurements) of a first pig of the two piglets obtained during an EIT process (e.g., described above in regard to FIGS. 1-3), and the window during which at least one initial impedance image was reconstructed via any of the manners described above. The same process was applied to the second pig of the two piglets. Furthermore, CT-scans were acquired from each of the two piglets. FIGS. 15 and 16 show an example CT-scan at a center of the electrode belt of one of the first piglet, and a reconstructed initial impedance image of the first piglet, respectively. FIGS. 17A-17E show additional reconstructed impedance images of the first piglet at different applied positive end expiratory pressure (PEEP) levels. FIGS. 18A-18F show reconstructed impedance images of the second piglet at various applied PEEP levels.

Referring to FIGS. 15-17E, for the first piglet, the heart was displaced compared to the anatomical atlas information; therefore, the reconstructed initial impedance image followed a true position instead of the prior information position.

Table 2 shows the functional residual capacity (FRC) of the first and second piglets determined from the CT-scans of the first and second piglets.

TABLE 2

| Piglet | Applied PEEP (20 cm H2O) | FRC (Volume (ml)) |
|---|---|---|
| First | 20 | 304.402679 |
| First | 10 | 238.545776 |
| First | 00 | 110.092323 |
| Second | 20 | 337.35955 |
| Second | 12 | 300.465758 |
| Second | 00 | 179.143632 |

Figure 19A:
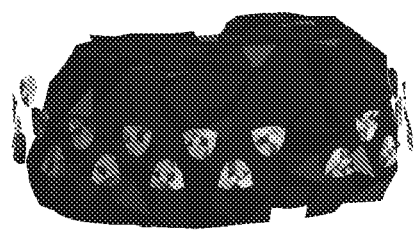
FIGS. 19A-19C show depictions of lungs regions identified by applying a threshold on the mean conductivity distribution of prior information and removing portions of the reconstructed initial impedance images not meeting the threshold.
Figure 19B:
Figure 19C:
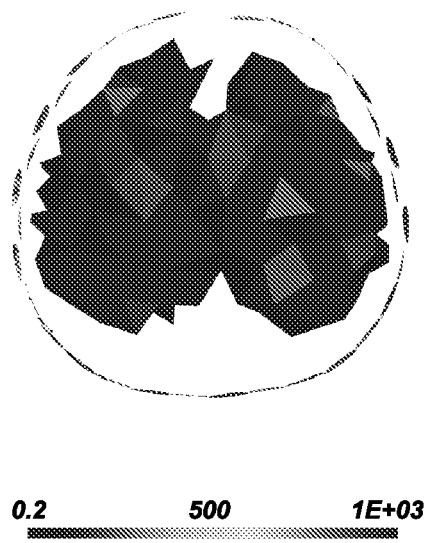

The lungs regions within the reconstructed initial impedance images of the first and second piglets were identified by applying a threshold on the mean conductivity distribution of the prior information and removing portions of the reconstructed initial impedance images not meeting the threshold, as depicted in FIGS. 19A-19C. An additional threshold was applied to remove the heart region from the reconstructed initial impedance images.

Furthermore, the weighted sum model of the lungs region can be determined via:

$$V_{EIT} = \Sigma(\rho_i v_i) \tag{20}$$

as discussed above in regard to FIGS. 9A and 9B, where $\rho_i$ is an electrical resistivity distribution represented in an enhanced impedance image of the region of interest, and $v_i$ is a tetrahedron volume of a Finite Element Mesh representation of the region of interest.

Continuing with methods described above in regard to FIGS. 9A and 9B, a first order correction was applied to estimate a fluid volume ($V_{fluid}$) via the following linear model:

$$V_{fluid} = a \cdot V_{EIT} + b \tag{21}$$

Variables a and b may be calculated (e.g., estimated) by relating an air content ($V_{fluid}$) estimated from prior information (e.g., CT-scans of another piglet (e.g., the second piglet)). In particular, the $V_{EIT(first)}$ of the first piglet may be determined and linear correction applied (e.g., variables a and b) to align with the $V_{fluid(first)}$ determined from the CT-scans of the first piglet. Thereafter, the $V_{fluid(second)}$ is determined by using $V_{EIT\ (second)}$ and the determined linear correction (e.g., variables a and b) from the first piglet. Additionally, the above process was repeated using the second piglet to determine variables a and b and the associated linear correction.

Table 3 shows the air volume estimation of the first piglet when using the first piglet to determine variables a and b, where a=2.3134e+05 and b=−1.537e+02.

TABLE 3

|  | PEEP20 | PEEP10 | PEEP00 |
|---|---|---|---|
| $V_{EIT}$ ($\Omega m^4$) | 1.8524e-03 | 1.4592e-03 | 1.0075e-03 |
| $V_{air}$ (ml) | 313.1495 | 222.1831 | 117.7082 |
| $V_{CT}$ (ml) | 304.4027 | 238.5458 | 110.0923 |
| Error (%) | 2.8 | -6.8 | 6.9 |

Table 4 shows the air volume estimation of the second piglet when using the first piglet to determine variables a and b.

TABLE 4

|  | PEEP20 | PEEP10 | PEEP00 |
|---|---|---|---|
| $V_{EIT}$ ($\Omega m^4$) | 2.1075e-03 | 1.9848e-03 | 1.3564e-03 |
| $V_{air}$ (ml) | 372.1654 | 343.7934 | 198.4187 |
| $V_{CT}$ (ml) | 337.3596 | 300.4658 | 179.1436 |
| Error (%) | 10.3 | 14.4 | 10.7 |

Table 5 shows the air volume estimation of the second piglet when using the second piglet to determine variables a and b, where a=2.0492e+05 and b=-9.9857e+01.

TABLE 5

|  | PEEP20 | PEEP10 | PEEP00 |
|---|---|---|---|
| $V_{EIT}$ ($\Omega m^4$) | 2.1075e-03 | 1.9848e-03 | 1.3564e-03 |
| $V_{air}$ (ml) | 332.0014 | 306.8697 | 178.0979 |
| $V_{CT}$ (ml) | 337.3596 | 300.4658 | 179.1436 |
| Error (%) | -1.5 | 2.1 | -0.5 |

Table 6 shows the air volume estimation of the second piglet when using the first piglet to determine variables a and b.

TABLE 6

|  | PEEP20 | PEEP10 | PEEP00 |
|---|---|---|---|
| $V_{EIT}$ ($\Omega m^4$) | 1.8524e-03 | 1.4592e-03 | 1.0075e-03 |
| $V_{air}$ (ml) | 279.7255 | 199.1482 | 106.6052 |
| $V_{CT}$ (ml) | 304.4027 | 238.5458 | 110.0923 |
| Error (%) | -8.1 | 16.5 | -3.1 |

Referring to FIGS. 1-19C together, the methods of determining volume estimations described herein may be advantageous. In particular, by enhancing the impedance images per the methods described herein, more accurate absolute impedance images may be generated in comparison to conventional absolute impedance images. For example, due to the anatomical atlases and prior information and enhancement methods described herein, the enhanced absolute impedance images described herein may be more accurate than conventional absolute impedance images. Additionally, the methods described herein using prior information improves organ localization during D-bar, iterative (e.g., Monte Carlo), and Kalman filter methods.

Determining the absolute impedance images and fluid volume estimates in the methods described herein may enable air volume estimation, cellularity on pleural effusions and pneumothorax volume determination, heart stroke volume estimation, total thoracic air volume determination, FRC, etc.

Figure 20:
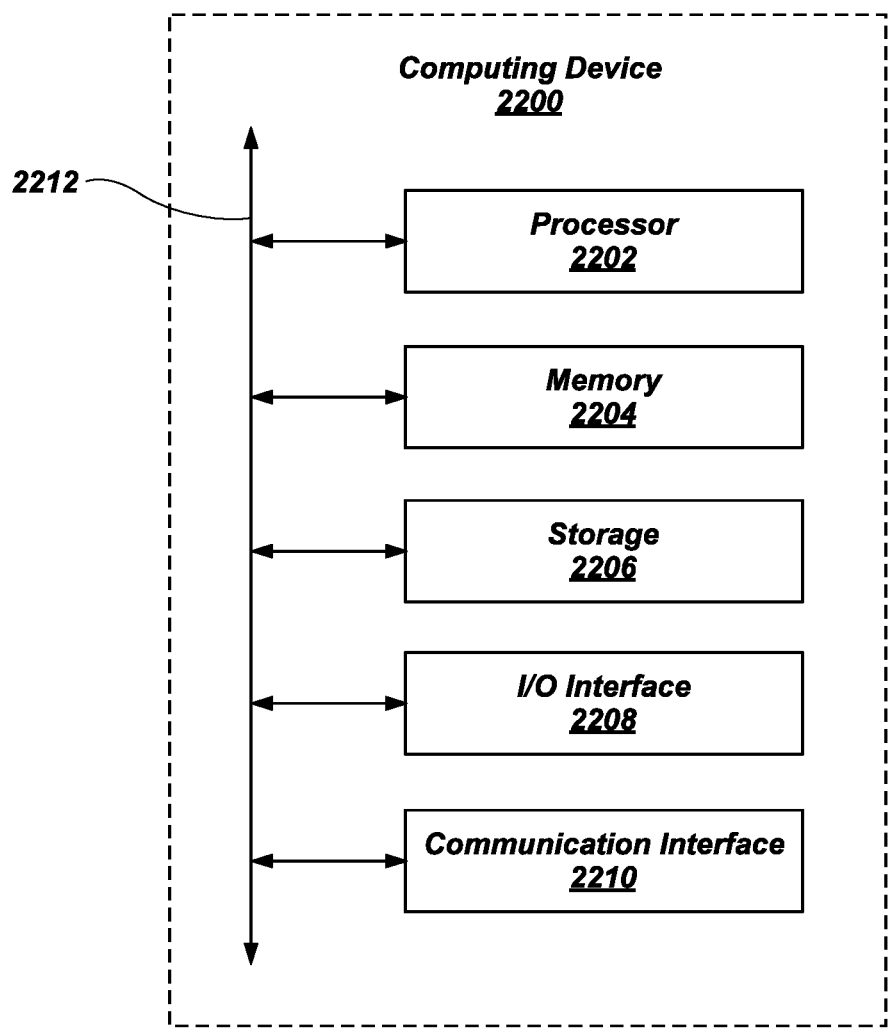
FIG. 20 illustrates a block diagram of an example volume estimation system that may be configured to perform one or more of the processes described above.

FIG. 20 illustrates a block diagram of an example volume estimation system 2200 that may be configured to perform one or more of the processes described above. One will appreciate that one or more computing devices may form the volume estimation system 2200. As shown by FIG. 20, the volume estimation system 2200 can comprise a processor 2202, a memory 2204, a storage device 2206, an I/O interface 2208, and a communication interface 2210, which may be communicatively coupled by way of a communication infrastructure. While an example volume estimation system 2200 is shown in FIG. 20, the components illustrated in FIG. 20 are not intended to be limiting. Additional or alternative components may be used in other embodiments. Furthermore, in certain embodiments, the volume estimation system 2200 can include fewer components than those shown in FIG. 20. Components of the volume estimation system 2200 shown in FIG. 20 will now be described in additional detail.

In one or more embodiments, the processor 2202 includes hardware for executing instructions, such as those making up a computer program. As an example, and not by way of limitation, to execute instructions, the processor 2202 may retrieve (or fetch) the instructions from an internal register, an internal cache, the memory 2204, or the storage device 2206 and decode and execute them. In one or more embodiments, the processor 2202 may include one or more internal caches for data, instructions, or addresses. As an example, and not by way of limitation, the processor 2202 may include one or more instruction caches, one or more data caches, and one or more translation look aside buffers (TLBs). Instructions in the instruction caches may be copies of instructions in the memory 2204 or the storage device 2206.

The volume estimation system 2200 includes memory 2204, which is coupled to the processor(s) 822. The memory 2204 may be used for storing data, metadata, and programs for execution by the processor(s). The memory 2204 may include one or more of volatile and non-volatile memories, such as Random-Access Memory ("RAM"), Read-Only Memory ("ROM"), a solid state disk ("SSD"), Flash, Phase Change Memory ("PCM"), or other types of data storage. The memory 2204 may be internal or distributed memory.

The volume estimation system 2200 includes a storage device 2206 that includes storage for storing data or instructions. As an example, and not by way of limitation, storage device 2206 can comprise a non-transitory storage medium described above. The storage device 2206 may include a hard disk drive (HDD), a floppy disk drive, Flash memory, an optical disc, a magneto-optical disc, magnetic tape, or a Universal Serial Bus (USB) drive or a combination of two or more of these. The storage device 2206 may include removable or non-removable (or fixed) media, where appropriate. The storage device 2206 may be internal or external to the volume estimation system 2200. In one or more embodiments, the storage device 2206 is non-volatile, solid-state memory. In other embodiments, the storage device 2206 includes read-only memory (ROM). Where appropriate, this ROM may be mask programmed ROM, programmable ROM (PROM), erasable PROM (EPROM), electrically erasable PROM (EEPROM), electrically alterable ROM (EAROM), or Flash memory or a combination of two or more of these.

The volume estimation system 2200 also includes one or more input or output ("I/O") devices/interfaces 2208 (e.g., a touch display), which are provided to allow a user to provide input to, receive output from, and otherwise transfer data to and receive data from volume estimation system 2200. The I/O devices/interfaces 2208 may include a mouse, a keypad or a keyboard, a touch screen, a camera, an optical scanner, network interface, modem, other known I/O devices or a combination of such I/O device/interfaces. The touch screen may be activated with a stylus or a finger.

The I/O devices/interfaces 2208 may include one or more devices for presenting output to a user, including, but not limited to, a graphics engine, a display (e.g., a display screen), one or more output drivers (e.g., display drivers), one or more audio speakers, and one or more audio drivers. In certain embodiments, the I/O interface 2208 is configured to provide graphical data to a display for presentation to a user. The graphical data may be representative of one or more graphical user interfaces and/or any other graphical content as may serve a particular implementation.

The volume estimation system 2200 can further include a communication interface 2210. The communication interface 2210 can include hardware, software, or both. The communication interface 2210 can provide one or more interfaces for communication (such as, for example, packet-based communication) between the volume estimation system 2200 and one or more other computing devices or networks. As an example, and not by way of limitation, the communication interface 2210 may include a network interface controller (NIC) or network adapter for communicating with an Ethernet or other wire-based network or a wireless NIC (WNIC) or wireless adapter for communicating with a wireless network, such as a WI-FI and/or Bluetooth. The volume estimation system 2200 can further include a bus 2212. The bus 2212 can comprise hardware, software, or both that couples components of volume estimation system 2200 to each other.

Embodiments of the present disclosure further include the following embodiments:

Embodiment 1. A method of estimate a fluid volume, the method comprising: receiving electrical tomography data of a portion of a domain; reconstructing an initial impedance image based at least partially on the electrical tomography data; enhancing the initial impedance image to generate an enhanced impedance image; segmenting the enhanced impedance image to identify one or more tissues depicted within the enhance impedance image; selecting a region of interest within the enhanced impedance image; determining a relationship parameter that relates electrical properties represented within the region of interest of the enhanced impedance image with one or more properties of the region of interest; and estimating a fluid volume within the region of interest based at least partially on the relationship parameter and the enhanced impedance image.

Embodiment 2. The method of embodiment 1, further comprising removing one or more portions outside of the region of interest of the enhanced impedance image from the enhanced impedance image.

Embodiment 3. The method of embodiment 2, wherein removing the one or more portions comprises removing portions of the enhanced impedance image that do not meet a threshold electrical property value.

Embodiment 4. The method of any one of embodiments 1-3, wherein the one or more properties comprise one or more of air content, blood content, or tissue content.

Embodiment 5. The method of any one of embodiments 1-4, further comprising: receiving prior information; determining a fluid content indicated in the prior information; correlating the fluid content indicated in the prior information to the relationship parameter; and estimating the fluid volume within the region of interest based at least partially on the received prior information.

Embodiment 6. The method of embodiment 5, wherein the received prior information comprises one or more CT-scans of the domain.

Embodiment 7. The method of embodiment 5, wherein the prior information comprises image data of one or more anatomy and physiology models.

Embodiment 8. The method of embodiment 5, further comprising selecting prior information to receive based one or more of anthropometric measures of the domain.

Embodiment 9. The method of embodiment 5, further comprising segmenting the enhanced impedance image to identify objects depicted in the prior information.

Embodiment 10. The method of any one of embodiments 1-9, wherein estimating the fluid volume within the region of interest comprises estimating an air volume within at least a portion of lungs of the domain.

Embodiment 11. The method of embodiment 10, wherein estimating the air volume comprises estimating an absolute air volume.

Embodiment 12. The method of embodiment 11, wherein reconstructing the initial impedance image comprises reconstructing an initial absolute impedance image.

Embodiment 13. The method of embodiment 11, wherein reconstructing the initial impedance image comprises reconstructing an initial difference impedance image.

Embodiment 14. The method of any one of embodiments 1-13, further comprising outputting a representation of the estimated fluid.

Embodiment 15. The method of claim 14, wherein the representation comprises a volumetric image comprising a plurality of pixels, voxels, or elements of a finite element mesh, wherein each pixel, voxel, or element of the finite element mesh represents a fluid volume.

Embodiment 16. A system comprising: an electrical tomography system; a volume estimate system comprising: at least one processor; and at least one non-transitory computer-readable storage medium storing instructions thereon that, when executed by the at least one processor, cause the volume estimation system to: reconstruct an initial impedance image based at least partially on received electrical tomography data of a domain; receive prior information associated with the domain; enhance the initial impedance image based at least partially on the received prior information to generate an enhanced impedance image; and based at least partially on the enhanced initial impedance image, generate a volumetric image of a region of interest of the enhanced impedance image, wherein the volumetric image represents a plurality of values indicating a volume of a fluid.

Embodiment 17. The system of claim 16, wherein the volumetric image is constructed of a plurality of pixels, voxels, or elements of a finite element mesh, wherein each pixel, voxel, of element of the finite element mesh represents a fluid volume.

Embodiment 18. The system of any one of embodiments 16 or 17, wherein reconstructing the initial impedance image comprises reconstructing an initial absolute impedance image.

Embodiment 19. The system of any one of embodiments 16-18, further comprising instructions that, when executed by the at least one processor, cause the volume estimation system to segment images in the prior information.

Embodiment 20. A system comprising: an electrical tomography system; a volume estimate system comprising: at least one processor; and at least one non-transitory computer-readable storage medium storing instructions thereon that, when executed by the at least one processor, cause the volume estimation system to: receive prior information associated with a domain; receive an initial impedance image of a portion of the domain from the electrical tomography system; enhance an initial impedance image based at least partially on the received prior information to generate an enhanced impedance image; and based at least partially on the enhanced initial impedance image, generate a volumetric image of a region of interest of the enhanced impedance image, wherein the volumetric image represents a plurality of values indicating a volume of a fluid.

While the disclosure has been described herein with respect to certain illustrated embodiments, those of ordinary skill in the art will recognize and appreciate that it is not so limited. Rather, many additions, deletions, and modifications to the illustrated embodiments may be made without departing from the scope of the invention as claimed, including legal equivalents thereof. In addition, features from one embodiment may be combined with features of another embodiment while still being encompassed within the scope of the disclosure as contemplated by the inventors. Further, embodiments of the disclosure have utility with different and various tool types and configurations.

What is claimed is:

1. A method of estimating a fluid volume, the method comprising:
   receiving electrical tomography data of a portion of a domain;
   reconstructing an initial impedance image based at least partially on the electrical tomography data;
   enhancing the initial impedance image to generate an enhanced impedance image;
   segmenting the enhanced impedance image to identify one or more tissues depicted within the enhanced impedance image;
   selecting a region of interest within the enhanced impedance image;
   determining a relationship parameter that relates electrical properties represented within the region of interest of the enhanced impedance image with one or more properties of the region of interest; and
   estimating a fluid volume within the region of interest based at least partially on the relationship parameter and the enhanced impedance image.

2. The method of claim 1, further comprising removing one or more portions outside of the region of interest of the enhanced impedance image from the enhanced impedance image.

3. The method of claim 2, wherein removing the one or more portions comprises removing portions of the enhanced impedance image that do not meet a threshold electrical property value.

4. The method of claim 1, wherein the one or more properties comprise one or more of air content, blood content, or tissue content.

5. The method of claim 1, further comprising:
   receiving prior information;
   determining a fluid content indicated in the prior information;
   correlating the fluid content indicated in the prior information to the relationship parameter; and
   estimating the fluid volume within the region of interest based at least partially on the received prior information.

6. The method of claim 5, wherein the received prior information comprises one or more CT-scans of the domain.

7. The method of claim 5, wherein the prior information comprises image data of one or more anatomy and physiology models.

8. The method of claim 5, further comprising selecting prior information to receive based one or more anthropometric measurement of the domain.

9. The method of claim 5, further comprising segmenting the enhanced impedance image to identify objects depicted in the prior information.

10. The method of claim 1, wherein estimating the fluid volume within the region of interest comprises estimating an air volume within at least a portion of lungs of the domain.

11. The method of claim 10, wherein estimating the air volume comprises estimating an absolute air volume.

12. The method of claim 11, wherein reconstructing the initial impedance image comprises reconstructing an initial absolute impedance image.

13. The method of claim 11, wherein reconstructing the initial impedance image comprises reconstructing an initial difference impedance image.

14. The method of claim 1, further comprising outputting a representation of the estimated fluid volume.

15. The method of claim 14, wherein the representation comprises a volumetric image comprising a plurality of pixels, voxels, or elements of a finite element mesh, wherein each pixel, voxel, or element of the finite element mesh represents a fluid volume.

16. The method of claim 1, wherein enhancing the initial impedance image to generate an enhanced impedance image comprises enhancing the initial impedance image through a D-bar method.

17. The method of claim 1, further comprising determining a regularization term based on the prior information, wherein reconstructing the initial impedance image comprises reconstructing the initial impedance image based at least partially on the regularization term.

18. A system comprising:
   an electrical tomography system;
   a volume estimation system comprising:
      at least one processor; and
      at least one non-transitory computer-readable storage medium storing instructions thereon that, when executed by the at least one processor, cause the volume estimation system to:
         reconstruct an initial impedance image based at least partially on received electrical tomography data of a domain;
         receive prior information associated with the domain;
         enhance the initial impedance image based at least partially on the received prior information to generate an enhanced impedance image;
         determine a relationship parameter that relates electrical properties of the domain of the enhanced impedance image with one or more properties of the domain; and
         based at least partially on the enhanced impedance image and the relationship parameter, generate a volumetric image of a region of interest of the enhanced impedance image, wherein the volumetric image represents a plurality of values indicating a volume of a fluid.

19. The system of claim 18, wherein the volumetric image is constructed of a plurality of pixels, voxels, or elements of a finite element mesh, wherein each pixel, voxel, of element of the finite element mesh represents a fluid volume.

20. The system of claim 18, wherein reconstructing the initial impedance image comprises reconstructing an initial absolute impedance image.

21. The system of claim 18, further comprising instructions that, when executed by the at least one processor, cause the volume estimation system to segment images in the prior information.

22. A system comprising:
an electrical tomography system;
a volume estimation system comprising:
  at least one processor; and
  at least one non-transitory computer-readable storage medium storing instructions thereon that, when executed by the at least one processor, cause the volume estimation system to:
    receive prior information associated with a domain;
    receive an initial impedance image of a portion of the domain from the electrical tomography system;
    enhance an initial impedance image based at least partially on the received prior information to generate an enhanced impedance image;
    determine a relationship parameter that relates electrical properties of the domain of the enhanced impedance image with one or more properties of the domain; and
    based at least partially on the enhanced impedance image and the relationship parameter, generate a volumetric image of a region of interest of the enhanced impedance image, wherein the volumetric image represents a plurality of values indicating a volume of a fluid.

* * * * *